US008697369B2

(12) United States Patent
Suzuki et al.

(10) Patent No.: US 8,697,369 B2
(45) Date of Patent: Apr. 15, 2014

(54) METHOD FOR SCREENING A TEST SUBSTANCE FOR ACTIVATING A RECEPTOR ASSOCIATED WITH FGF 21 ACTIVITY

(75) Inventors: Masashi Suzuki, Ibaraki (JP); Toru Imamura, Ibaraki (JP); Yuriko Uehara, Ibaraki (JP); Kaori Motomura, Ibaraki (JP); Junko Oki, Ibaraki (JP); Syuichi Oka, Ibaraki (JP); Masahiro Asada, Ibaraki (JP); Akiko Kuramochi, Ibaraki (JP); Miho Kimura, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 232 days.

(21) Appl. No.: 12/594,210

(22) PCT Filed: Apr. 7, 2008

(86) PCT No.: PCT/JP2008/056906
§ 371 (c)(1),
(2), (4) Date: Oct. 1, 2009

(87) PCT Pub. No.: WO2008/123625
PCT Pub. Date: Oct. 16, 2008

(65) Prior Publication Data
US 2010/0184665 A1 Jul. 22, 2010

(30) Foreign Application Priority Data

Apr. 6, 2007 (JP) ................................ 2007-100865
Jul. 12, 2007 (JP) ................................ 2007-182848
Aug. 24, 2007 (JP) ................................ 2007-218588

(51) Int. Cl.
*C12Q 1/68* (2006.01)
(52) U.S. Cl.
USPC ........................................ 435/7.21; 514/9.1
(58) Field of Classification Search
None
See application file for complete search history.

(56) References Cited

PUBLICATIONS

Kurosu et al. Mol. Cell Endocrinol. 299: 72-78, 2009.*
Kurosu et al. J. Biol. Chem. 282(37): 26687-26695, 2007.*
Givol et al. FASEB J. 6:3362-3369, 1992.*
Zhang et al. J. Biol. Chem. 281(23): 15694-15700, 2006.*
Suzuki et al. Mol. Endocrinol. 22(4): 1006-1014, 2008.*
Moyers, J. S., et al. "Molecular Determinants of FGF-21 Activity-Synergy and Cross-Talk with PPARγ Signaling." *Journal of Cellular Physiology* (2007) vol. 210, No. 1, pp. 1-6.
Urakawa, I., et al. "Klotho converts canonical FGF receptor into a specific receptor for FGF23."*Nature* (2006) vol. 444, No. 7120, pp. 770-774.
Kurosu, H., et al. "Regulation of Fibroblast Growth Factor-23 Signaling by Klotho."*Journal of Biological Chemistry* (2006) vol. 281, No. 10, pp. 6120-6123.
Fukumoto, S., et al. "FGF23 is a hormone-regulating phosphate metabolism—Unique biological characteristics of FGF23." *BONE* (2007) vol. 40, No. 5, pp. 1190-1195.
Goetz, R., et al. "Molecular Insights into the Klotho-Dependent, Endocrine Mode of Action of Fibroblast Growth Factor 19 Subfamily Members." *Molecular and Cellular Biology* (2007) vol. 27, No. 9, pp. 3417-3428.
Ito, S., et al. "Molecular cloning and expression analyses of mouse βklotho, which encodes a novel Klotho family protein." *Mechanisms of Development* (2000) vol. 98, No. 1, pp. 115-119.
Ogawa, Y., et al. "βKlotho is required for metabolic activity of fibroblast growth factor 21." *PNAS* (2007) vol. 104, No. 18, pp. 7432-7437.
Kharitonenkov, A., et al. "FGF-21 as a novel metabolic regulator."*Journal of Clinical Investigation* (2005) vol. 115, No. 6, pp. 1627-1635.
Itoh, N., et al. "Evolution of the Fgf and Fgfr gene families."*TRENDS* (2004) vol. 20, No. 11, pp. 563-569.
Inagaki, T., et al. "Fibroblast growth factor 145 functions as an enterohepatic signal to regulate bile acid homeostasis." *Cell Metabolism* (2005) vol. 2, pp. 217-225.
Yu, X., et al. "FGF23 and disorders of phosphate homeostasis." *Cytokine & Growth Factor Reviews* (2005) vol. 16, pp. 221-232.
Kharitonenkov, A., et al. "The Metabolic State of Diabetic Monkeys is Regulated by Fibroblast Growth Factor-21." *Endocrinology* (2007) vol. 148, No. 2, pp. 774-781.
Wente, W., et al. "Fibroblast Growth Factor-21 Improves Pancreatic β-Cell Function and Survival by Activation of Extracellular Signal-Regulated Kinase ½ and Akt Signaling Pathways."*Diabetes* (2006) vol. 55, No. 9, pp. 2470-2478.
Ito, S., et al. "Impaired negative feedback suppression of bile acid synthesis in mice lacking βKlotho." *Journal of Clinical Investigation* (2005) vol. 115, No. 8, pp. 2202-2208.
Nishimura, T., et al. "Identification of a novel FGF, FGF-21, preferentially expressed n the liver."*Biochimica et Biophysica Acta* 1492 (2000) pp. 203-206.
LeSauteur, L., et al. "Potent Human p140-TrkA Agonists Derived from an Anti-Receptor Monoclonal Antibody." *Journal of Neuroscience* (1996) 16(4), pp. 1308-1316.
Fernandez-Pol, J. A.. "Epidermal Growth Factor Receptor of A431 Cells." *Journal of Biological Chemistry* (1985) vol. 260, No. 8, pp. 5003-5011.

\* cited by examiner

*Primary Examiner* — Christine J Saoud
(74) *Attorney, Agent, or Firm* — Ladas & Parry LLP

(57) ABSTRACT

Using betaKlotho or a substance that increases or inhibits betaKlotho activity as an agent for controlling the activity of FGF21 mediated by an FGF receptor, the present invention provides a pharmaceutical composition comprising such betaKlotho or such substance as an active ingredient, particularly, a pharmaceutical composition for anti-metabolic syndrome, and further particularly, a pharmaceutical composition for therapeutic or preventive use associated with the control of blood glucose level. In addition, the present invention provides a screening system for each of a substance that enhances or suppresses betaKlotho activity, an FGF21-like active substance, and a betaKlotho-like active substance, which uses a cell system that has expressed an FGF receptor and/or betaKlotho on the surface thereof.

1 Claim, 16 Drawing Sheets

A)

IP: anti-V5-beads (to pull-down βKlotho)

B)

IP: proteinA-beads (to pull-down FGFR-Fc)

METHOD FOR SCREENING A TEST SUBSTANCE FOR ACTIVATING A RECEPTOR ASSOCIATED WITH FGF 21 ACTIVITY

FIELD OF THE INVENTION

The present invention relates to a method for promoting or suppressing the activation of a receptor by a ligand, using a co-receptor, a gene encoding the co-receptor, or a substance that enhances or suppresses the activity of the co-receptor, and a method for regulating ligand activity (and a method for controlling blood glucose level using the same).

DESCRIPTION OF RELATED ART

With regard to high blood glucose level, which is considered to be problematic for diabetes, it is necessary to understand a mechanism for controlling blood glucose level in a health body and to utilize such knowledge to regulate the blood glucose level to a normal value. However, such mechanism for regulating blood glucose level in a body has not yet been clarified. An active treatment method, which is practically used at present, is only a method comprising administering insulin to a patient with diabetes and thereby decreasing his/her blood glucose level to a normal range, utilizing the action of the insulin to decrease blood glucose level. This treatment method is extremely effective for patients with diabetes caused by an insufficient amount of insulin secreted. However, even if insulin is administered to patients with diabetes, some patients do not respond thereto and thus their blood glucose level is not decreased. It is urgent to develop a diabetes drug, which is effective even for such, what are called, insulin-resistant patients. Therefore, it is a significant object in the present technical field to clarify a mechanism for regulating blood glucose level in a body so as to solve the aforementioned problem.

By the way, based on amino acid sequence homology and structural similarity, it has been known that, at present, 22 types of FGF family molecular groups known as fibroblast growth factors (FGF) exist in a human and a mouse. Not all the FGF family members have been clarified in terms of active function. However, several FGF family members whose functions have been vigorously studied are known to have not only fibroblast-proliferative activity but also the activity of regulating the growth or differentiation of a variety of cells. Such members are factor groups deeply involved in various types of life phenomena such as morphogenesis, angiogenesis, the maintenance of neuronal survival, and metabolic regulation (Non-Patent Documents 1, 2, 3, and 4). Among such members, FGF19, FGF21, and FGF23, which have been relatively recently added to the FGF family group, form subgroups similar to one another from the viewpoint of domain structure and amino acid sequence homology. However, it cannot be said that the mechanism of action of these FGF members has been sufficiently clarified. In addition, even if such FGF members are subjected to an assay system for measuring cell growth or differentiation, which has been commonly used for the general FGF family, almost no activity is detected.

Recently, it has been reported that FGF21 acts to enhance the expression level of a glucose transporter of an adipocyte so as to increase the uptake of glucose in the cell, that intravenous or subcutaneous administration of FGF21 causes a decrease in blood glucose level at an individual animal level, that it suppresses blood triglyceride level, and that it decreases LDL cholesterol level and increases HDL cholesterol level (Non-Patent Documents 1 and 5). Moreover, it has also been reported that FGF21 acts on the islets of Langerhans in the pancreas, so as to increase the amount of insulin synthesized (Non-Patent Document 6). From these reports, FGF21 has been considered to play an important role for the control of blood glucose level or the control of neutral fat level, and thus it has attracted attention as a candidate for an agent for treating metabolic syndrome having a new mechanism of action.

However, in order to use FGF21 as a therapeutic agent for metabolic syndrome, single application of FGF21 is not sufficient, and thus it is essential to search for a factor for increasing the action of FGF21. However, a factor that effectively increases the action has not yet been discovered.

In general, in order for FGF to exhibit its activity, it is necessary for the FGF to bind to an FGF receptor on the surface of cell membrane to activate it, so as to provoke intracellular signaling. In the case of FGF21 as well, it has been reported that, when the FGF21 is allowed to act on an adipocyte, the activation of FGFR1 and FGFR2 existing on the cell surface occurs (Non-Patent Document 1). Blood glucose level-lowering action observed in FGF21 is considered to result from signaling based on the interaction of the FGF21 with these FGF receptors. If the mechanism of FGF21 for activating FGF receptors were clarified, blood glucose level could be controlled using factors associated with such mechanism. Nevertheless, the conventional findings have not been directly used to clarify the binding manner of FGF21 to FGF receptors or the mechanism for controlling blood glucose level, such as a glucose transporter or insulin expression. Hence, the conventional findings have not been used to provide such factors capable of controlling blood glucose level.

Accordingly, in the present field, it has become a major issue to rapidly clarify how FGF21 activates FGF receptors and to establish a method for controlling the function of the FGF21 to regulate blood glucose level and the like, thereby providing an effective therapeutic agent for metabolic syndrome, which comprises the FGF21 as an active ingredient.

Non-Patent Document 1
Kharitonenkov, A., Shiyanova, T. L., Koester, A., Ford, A M., Micanovic, R., Galbreath, E. 1., Sandusky, G. E., Hammond, L. 1., Moyers, J. S., Owens, R. A., Gromada, J., Brozinick, J. T., Hawkins, E. D., Wroblewski, V. J., Li, D. S., Mehrbod, F., Jaskunas, S. R., and Shanafelt, A. B. (2005) J Clin Invest 115(6), 1627-1635

Non-Patent Document 2
Itoh, N. and Ornitz, D. M. (2004) Evolution of the Fgf and Fgfr gene families. Trends Genet, 20, 563-569.

Non-Patent Document 3
Inagaki, T., Choi, M., Moschetta, A, Peng, L., Cummins, C. L., McDonald, J. G., Luo, G., Jones, S. A, Goodwin, B., Richardson, J. A, Gerard, R. D., Repa, 1. J., Mangelsdorf, D. J. and Kliewer, S. A. (2005) Fibroblast growth factor 15 functions as an enterohepatic signal to regulate bile acid homeostasis. Cell Metab, 2, 217-225.

Non-Patent Document 4
Yu, X. and White, K. E. (2005) FGF23 and disorders of phosphate homeostasis. Cytokine Growth Factor Rev, 16,221-232.

Non-Patent Document 5
Kharitonenkov, A., Wroblewski, V. J., Koester, A, Chen, Y. F., Clutinger, C. K., Tigno, X. T., Hansen, B. C., Shanafelt, A. B., and Etgen, G. J. (2007) Endocrinology 148(2), 774-781

Non-Patent Document 6
Wente, W., Efanov, A. M., Brenner, M., Kharitonenkov, A., Koster, A., Sandusky, G. E., Sewing, S., Treinies, I., Zitzer, H., and Gromada, J. (2006)

Diabetes 55(9), 2470-2478

Non-Patent Document 7

Ito, S., Fujimori, T., Furuya, A, Satoh, J., Nabeshima, Y., and Nabeshima, Y. (2005) J Clin Invest 115(8), 2202-2208

Non-patent Document 8

Ito, S., Kinoshita, S., Shiraishi, N., Nakagawa, S., Sekine, S., Fujimori, T. and Nabeshima, Y J. (2000) Molecular cloning and expression analyses of mouse betaklotho, which encodes a novel Klotho family protein. Mech Dev, 98, 115-119.

Non-Patent Document 9

Nishimura, T., Nakatake, Y., Konishi, M. and Itoh, N. (2000) Identification of a novel FGF, FGF-21, preferentially expressed in the liver. Biochim Biophys Acta, 1492, 203-206

Non-Patent Document 10

LeSauteur, L. et al. (1996) J Neurosci, 16, 1308-1316)

Non-Patent Document 11

Fernandez-Pol, 1A. (1985) J Biol Chem, 260, 5003-5011)

Patent Document 1

JP Patent Publication (Kokai) No. 2006-158339, which is a patent publication relevant to Non-Patent Document 7

Patent Document 2

U.S. Pat. No. 6,099,841

Patent Document 3

U.S. Pat. No. 6,365,154

SUMMARY OF THE INVENTION

It is an object of the present invention to provide an effective factor for controlling the activity of FGF21 mediated by an FGF receptor. Typically, it is an object of the present invention to provide a method for identifying a co-receptor that is necessary when the uptake of glucose in a cell is controlled by FGF21, a method for regulating the activity of FGF21 utilizing the aforementioned co-receptor, and a method for controlling blood glucose level using the aforemetnioned activity.

In addition, it is another object of the present invention to provide: an agent for controlling the activity of FGF21, which comprises, as an active ingredient(s), the aforementioned controlling factor and/or a substance that increases or suppresses the activity thereof; and a pharmaceutical composition for controlling the activity of FGF21 mediated by an FGF receptor, for example, a pharmaceutical composition for treating or preventing diseases associated with abnormal uptake of glucose including an abnormal increase or decrease in blood glucose level, such as diabetes.

Moreover, it is a further object of the present invention to provide a screening system, which screens for a factor for controlling the activity of FGF21 mediated by an FGF receptor, a substance that increases or suppresses the activity of the aforementioned controlling factor, and an FGF21-like active substance.

As a result of intensive studies directed towards achieving the aforementioned objects, the present inventor found that betaKlotho is a specific co-receptor, which is necessary when the uptake of glucose in a cell is controlled by FGF21.

Specifically, in order to confirm how FGF21 activates an FGF receptor and conditions necessary for the activation of such receptor, the present inventors first prepared multiple cells that expressed each FGF receptor on the surface thereof, which generally does not have the FGF receptor, and they then allowed the cells to react with FGF21. As a result, the inventors discovered that the activation of such FGF receptor was not detected in all cases, even using FGF21 in a concentration that is several tens to several hundreds higher than the concentration in which, in general, FGF1 sufficiently exhibits its activity.

Since heparin acting as a receptor cofactor is essential when an ordinary FGF ligand binds to each FGF receptor, heparin was further added to the aforementioned system, and it was then observed. However, even in the presence of such heparin, the activation of the FGF receptor did not occur as in the absence of heparin. Thus, the present inventors conducted intensive studies regarding the way in which FGF21 activates an FGF receptor and necessary conditions therefor. In such study process, the inventors discovered that FGFR1c is activated by FGF21 when betaKlotho is also present on the membrane, and that a downstream signal is provoked.

Subsequently, the present inventors carried out an experiment using various types of transformed cell systems, which were produced by introducing an FGFR1c gene or an FGFR3c gene, or further, a betaKlotho gene and a Klotho gene that is a structural homolog thereof into a BaF3 cell that endogenously expressed neither an FGF receptor nor betaKlotho, and then by allowing such genes to express on the cell surface. The inventors observed whether or not they were still compatible even if the combination of FGF21 and betaKlotho with their structural homologs were changed. As a result, the inventors discovered that the combination of FGF21 with betaKlotho is a specific combination with regard to the action on FGFR1c or FGFR3c. That is to say, this result demonstrates that betaKlotho is a co-receptor specific to FGF21 in binding to FGF receptor.

The present inventors focused attention on that a transformed cell system, which is produced by introducing a betaKlotho gene, together with the aforementioned FGFR1c gene or FGFR3c gene, into a cell and then allowing them to express on the cell surface, extremely sensitively shows the degree of activation of an FGF receptor by FGF21, which is exhibited in the coexistence of the FGF receptor and betaKlotho. Based on such findings, the inventors were able to provide a screening system for a substance that enhances or suppresses betaKlotho activity and a screening system for an FGF21-like substance, which use the aforementioned transformed cell system. In addition, they were also able to provide a screening system for a substance exhibiting betaKlotho-like activity, which uses a transformed cell system produced by introducing only an FGFR1c gene or FGFR3c gene into a cell and allowing it to express on the surface thereof.

As described above, the present inventors found that the biological activity of FGF21 mediated by an FGF receptor can be regulated by the presence or absence of betaKlotho. Based on such findings, the inventors completed the present invention relating to an agent and a pharmaceutical composition for controlling the activity of FGF21 mediated by an FGF receptor, using betaKlotho and a substance that enhances or inhibits the activity thereof. At the same time, utilizing an excellent transformed cell system that was used at that time, the inventors also completed the present invention regarding various types of screening methods.

Specifically, the present invention includes the following features.

(1) An agent for controlling the activity of FGF21, which comprises, as an active ingredient, a protein having betaKlotho activity, and which is used to increase or suppress the biological activity of FGF21 mediated by an FGF receptor.

(2) The agent for controlling the activity of FGF21 according to (1) above, wherein the protein having betaKlotho activity is a soluble betaKlotho partial protein.

(3) An agent for controlling the activity of FGF21, which comprises, as an active ingredient, recombinant DNA containing DNA encoding a protein having betaKlotho activity, and which is used to increase or suppress the biological activity of FGF21 mediated by an FGF receptor.

(4) The agent for controlling the activity of FGF21 according to (3) above, wherein the DNA encoding a protein having betaKlotho activity is DNA encoding a betaKlotho soluble partial protein.

(5) An agent for controlling the activity of FGF21, which is used to increase or suppress the action of a protein having betaKlotho activity to control the activity of FGF21 mediated by an FGF receptor; wherein the agent is characterized in that it comprises, as an active ingredient, a substance that enhances or inhibits the betaKlotho activity.

(6) The agent for controlling the activity of FGF21 according to (5) above, wherein the substance that enhances the betaKlotho activity is heparin or a heparin-like substance.

(7) The agent for controlling the activity of FGF21 according to (5) above, wherein the substance that enhances or inhibits the betaKlotho activity is an anti-betaKlotho antibody.

(8) The agent for controlling the activity of FGF21 according to any one of (1) to (7) above, wherein the FGF receptor is FGFR1c or FGFR3c.

(9) The agent for controlling the activity of FGF21 according to any one of (1) to (8) above, wherein the biological activity of FGF21 mediated by an FGF receptor is any one of the enhancement of glucose uptake, a decrease in blood glucose level, the enhancement of expression of a glucose transporter, the enhancement of insulin expression, and the regulation of metabolism.

(10) A pharmaceutical composition for controlling the activity of FGF21 mediated by an FGF receptor, which comprises, as an active ingredient, a protein having betaKlotho activity or recombinant DNA containing DNA encoding the protein.

(11) The pharmaceutical composition according to (10) above, wherein the protein having betaKlotho activity is a betaKlotho soluble partial protein.

(12) A pharmaceutical for controlling the activity of FGF21 mediated by an FGF receptor, using a protein having betaKlotho activity, which is characterized in that it comprises, an active ingredient, a substance that enhances or inhibits the betaKlotho activity.

(13) The pharmaceutical composition according to (12) above, wherein the substance that enhances the betaKlotho activity is heparin or a heparin-like substance.

(14) The pharmaceutical composition according to (12) above, wherein the substance that enhances or inhibits the betaKlotho activity is an anti-betaKlotho antibody.

(15) The pharmaceutical composition according to any one of (10) to (14) above, which is characterized in that it comprises, as an active ingredient, a substance that enhances or inhibits the betaKlotho activity, as well as the protein having the betaKlotho activity or the recombinant DNA containing DNA encoding the protein.

(16) The pharmaceutical composition according to any one of (10) to (15) above, which further comprises FGF21 as an active ingredient.

(17) The pharmaceutical composition according to any one of (10) to (16) above, wherein the FGF receptor is FGFR1c or FGFR3c.

(18) The pharmaceutical composition according to any one of (10) to (17) above, wherein the pharmaceutical composition for controlling the activity of FGF21 mediated by an FGF receptor is used for any one of the enhancement of glucose uptake, a decrease in blood glucose level, the enhancement of expression of a glucose transporter, and the enhancement of insulin expression.

(19) A method for increasing or suppressing the biological activity of FGF21 mediated by an FGF receptor, which is characterized in that it uses the agent for controlling the activity of FGF21 according to any one of (1) to (9) above.

(20) The method for increasing or suppressing the biological activity of FGF21 mediated by an FGF receptor according to (19) above, wherein the FGF receptor is FGFR1c or FGFR3c.

(21) The method for increasing or suppressing the biological activity of FGF21 mediated by an FGF receptor according to (19) or (20) above, which is characterized in that it comprises allowing the agent for controlling the activity of FGF21, as well as FGF21, to act on the FGF receptor, so as to enhance or suppress the activation of the FGF receptor.

(22) The method for increasing or suppressing the biological activity of FGF21 mediated by an FGF receptor according to (19) or (20) above, which is characterized in that it comprises allowing the agent for controlling the activity of FGF21 to act on the FGF receptor in the coexistence of FGF21 and betaKlotho, so as to enhance or suppress the activation of the FGF receptor.

(23) A method for screening for a substance that increases or suppresses the biological activity of FGF21 mediated by an FGF receptor, using a transformed cell obtained by introducing an FGF receptor gene into a cell that has endogenously expressed neither the FGF receptor nor betaKlotho so as to allow the FGF receptor to express on the cell surface, wherein
the screening method is characterized in that it comprises:
a step of allowing FGF21 and a test substance to act on a culture system of the transformed cell expressing the FGF receptor on the surface thereof; or
a step of introducing an FGF receptor gene and a test substance gene into the cell that has endogenously expressed neither the FGF receptor nor betaKlotho, and then allowing FGF21 to act on a transformed cell system in which the test substance as well as the FGF receptor are allowed to express on the surface thereof.

(24) The screening method according to (23) above, which is characterized in that the cell that has endogenously expressed neither the FGF receptor nor betaKlotho is a BaF3 cell.

(25) The method for screening for a substance that increases or suppresses the biological activity of FGF21 according to (23) or (24) above, wherein the FGF receptor is FGFR1c or FGFR3c.

(26) A kit for screening for a substance that increases or suppresses the biological activity of FGF21 mediated by an FGF receptor, which is produced by combining a transformed cell system obtained by introducing an FGF receptor gene into a cell that has endogenously expressed neither the FGF receptor nor betaKlotho and then allowing the FGF receptor to express on the surface thereof with the FGF21.

(27) The screening kit according to (26) above, which is characterized in that the cell that has endogenously expressed neither the FGF receptor nor betaKlotho is a BaF3 cell.

(28) The kit for screening for a substance that increases or suppresses the biological activity of FGF21 according to (26) or (27) above, wherein the FGF receptor is FGFR1c or FGFR3c.

(29) A method for screening for a substance that enhances or inhibits betaKlotho activity associated with the action to control the activity of FGF21 mediated by an FGF receptor, using a culture system of a transformed cell obtained by introducing an FGF receptor gene and a betaKlotho gene into a cell that has endogenously expressed neither the FGF receptor nor betaKlotho so as to allow the FGF receptor and betaKlotho to express on the cell surface, wherein the screening method is characterized in that it comprises:

a step of allowing FGF21 and a test substance to act on a system of the transformed cell expressing the FGF receptor and betaKlotho on the surface thereof; or a step of introducing an FGF receptor gene and a betaKlotho gene as well as a test substance gene into a cell used as a host that has endogenously expressed neither the FGF receptor nor betaKlotho, and then allowing FGF21 to act on a transformed cell system in which the test substance as well as the FGF receptor and betaKlotho are allowed to express on the surface thereof.

(30) The screening method according to (29) above, which is characterized in that the cell that has endogenously expressed neither the FGF receptor nor betaKlotho is a BaF3 cell.

(31) The method for screening for a substance that enhances or inhibits betaKlotho activity associated with the action to control the activity of FGF21 according to (29) or (30) above, wherein the FGF receptor is FGFR1c or FGFR3c.

(32) A kit for screening for a substance that enhances or inhibits betaKlotho activity associated with the action to control the activity of FGF21 mediated by an FGF receptor, which is produced by combining a transformed cell system obtained by introducing an FGF receptor gene and a betaKlotho gene into a cell that has endogenously expressed neither the FGF receptor nor betaKlotho and allowing the FGF receptor and betaKlotho to express on the surface thereof with the FGF21.

(33) The screening kit according to (32) above, which is characterized in that the cell that has endogenously expressed neither the FGF receptor nor betaKlotho is a BaF3 cell.

(34) The kit for screening for a substance that enhances or inhibits betaKlotho activity associated with the action to control the activity of FGF21 according to (32) or (33) above, wherein the FGF receptor is FGFR1c or FGFR3c.

(35) A method for screening for an FGF21-like active substance, which is characterized in that it comprises a step of introducing an FGF receptor gene and a betaKlotho gene into a cell that has endogenously expressed neither the FGF receptor nor betaKlotho and then allowing a test substance to act on a transformed cell system expressing the FGF receptor and betaKlotho on the surface thereof.

(36) The screening method according to (35) above, which is characterized in that the cell that has endogenously expressed neither the FGF receptor nor betaKlotho is a BaF3 cell.

(37) The method for screening for an FGF21-like active substance according to (35) or (36) above, wherein the FGF receptor is FGFR1c or FGFR3c.

(38) A kit for screening for an FGF21-like active substance, which is characterized in that it uses a transformed cell system, which is obtained by introducing an FGF receptor gene and a betaKlotho gene into a cell that has endogenously expressed neither the FGF receptor nor betaKlotho so as to allow the FGF receptor and betaKlotho to expressed on the surface thereof.

(39) The screening kit according to (38) above, which is characterized in that the cell that has endogenously expressed neither the FGF receptor nor betaKlotho is a BaF3 cell.

(40) The kit for screening for an FGF21-like active substance according to (38) or (39) above, wherein the FGF receptor is FGFR1c or FGFR3c.

(41) An agent for controlling the activity of FGF21 used to increase or suppress the biological activity of FGF21 mediated by an FGF receptor, which is exhibited in the coexistence of the FGF receptor and betaKlotho; wherein the agent is characterized in that it comprises, as an active ingredient, a substance that increases or suppresses the biological activity of FGF21 mediated by an FGF receptor, obtained by the screening method according to any one of (23) to (25) above.

(42) An agent for controlling the activity of FGF21 used to increase or suppress the biological activity of FGF21 mediated by an FGF receptor, which is exhibited in the coexistence of the FGF receptor and betaKlotho; wherein the agent is characterized in that it comprises, as an active ingredient, a substance that enhances or inhibits betaKlotho activity associated with the action to control the activity of FGF21 mediated by an FGF receptor, obtained by the screening method according to any one of (29) to (31) above.

(43) An agent for activating an FGF receptor, which is characterized in that it comprises, as an active ingredient, an FGF21-like active substance obtained by the screening method according to any one of (35) to (37) above, and in that it acts on the FGF receptor in the coexistence of betaKlotho.

(44) A pharmaceutical composition for controlling the activity of FGF21 mediated by an FGF receptor, which is exhibited in the coexistence of the FGF receptor and betaKlotho; wherein the pharmaceutical composition is characterized in that it comprises, as an active ingredient, a substance that increases or suppresses the biological activity of FGF21 mediated by an FGF receptor, obtained by the screening method according to any one of (23) to (25) above.

(45) A pharmaceutical composition for controlling the biological activity of FGF21 mediated by an FGF receptor, which is exhibited in the coexistence of the FGF receptor and betaKlotho; wherein the pharmaceutical composition is characterized in that it comprises, as an active ingredient, a substance that enhances or inhibits betaKlotho activity associated with the action to control the activity of FGF21 mediated by the FGF receptor, obtained by the screening method according to any one of (29) to (31) above.

(46) A pharmaceutical composition for activating an FGF receptor, which is characterized in that it comprises, as an active ingredient, an FGF21-like active substance obtained by the screening method according to any one of (35) to (37) above, and in that it acts on the FGF receptor in the coexistence of betaKlotho.

According to the present invention, it is possible to regulate various reactions based on the interaction of FGF21 with an FGF receptor by controlling the activity of FGF21 mediated by an FGF receptor using a protein having betaKlotho activity, thereby provoking or suppressing a signal downstream of the FGF receptor. In addition, according to the present invention, the activity of FGF21 mediated by an FGF receptor, for example, blood glucose level-lowering action, can be controlled by administering a protein having betaKlotho activity or a substance that increases or inhibits such betaKlotho activity. Thus, using such protein having betaKlotho activity and such substance that increases or inhibits the betaKlotho activity, singly or in combination, or using such protein and substance in combination with FGF21, there can be provided a pharmaceutical composition for treating or preventing diseases associated with abnormal blood glucose level, such as diabetes.

Moreover, there can also be provided an excellent screening system for an FGF21-like active substance, an alternative substance to betaKlotho, and a substance that increases or inhibits the activity of betaKlotho.

BRIEF DESCRIPTION OF THE DRAWINGS

FIG. 4 is a view showing the results obtained by analyzing the necessity of betaKlotho for provocation of a signal downstream of an FGF receptor due to FGF21.

DETAILED DESCRIPTION OF THE INVENTION

Figure 1:
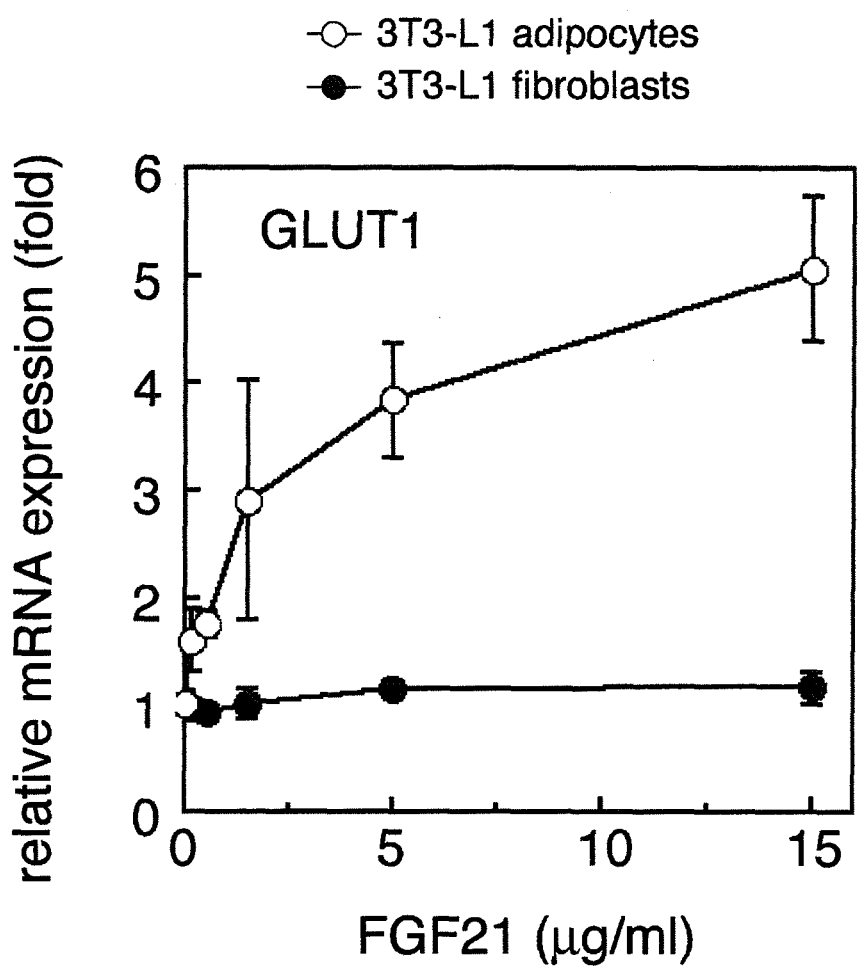
FIG. 1 is a view showing the detection results of the adipocyte-specific activity of FGF21. In the figure, the value obtained when each type of cells are not stimulated with FGF21 is defined as 1, and the level of GLUT1 mRNA is indicated as a value relative to the aforementioned value. The symbol ● indicates fibroblasts before differentiation, and the symbol ○ indicates adipocytes after differentiation. It was demonstrated that FGF21 acts on adipocytes obtained after differentiation from the 3T3-L1 cells, so as to increase GLUT1 expression, and that it does not act on the fibroblasts.

Hereinafter, the present invention will be described in detail in accordance with the embodiments of the present invention. However, the present invention is not limited by these embodiments.

[1] Concerning BetaKlotho

The present invention was made to clarify the action function of betaKlotho in vivo and to provide a method utilizing such betaKlotho.

BetaKlotho is a substance that has been cloned as a Klotho homolog (Non-Patent Document 8). The nucleotide sequence of a mouse-derived betaKlotho gene is shown in SEQ ID NO: 1, and the corresponding amino acid sequence is shown in SEQ ID NO: 2. The nucleotide sequence of a human-derived betaKlotho gene is shown in SEQ ID NO: 7, and the corresponding amino acid sequence is shown in SEQ ID NO: 8. It has been known that such betaKlotho is expressed in the adipocytes of a developing mouse fetus and the like. Methods for obtaining the gene from other organism species and methods for producing various types of modified bodies, mutants and the like are described in several publications (Non-Patent Documents 7 and 8, and Patent Document 1).

The aforementioned Non-Patent Document 7 and Patent Document 1 describe that a knockout mouse comprising a homozygous disruption of gene was produced and analyzed, and that as a result, such betaKlotho gene was found to be a "gene involved in cholesterol metabolism" and using this gene, a substance that promotes cholesterol metabolism could be obtained. However, these publications contain no descriptions for teaching the function of the gene associated with the control of blood glucose level or the relationship of the gene with the activity of FGF21.

On the other hand, it was discovered for the first time by the present invention that betaKlotho is a substance essential for a phenomenon whereby FGF21 binds to an FGF receptor to activate it thereby causing its signaling, and that such betaKlotho is a factor having important regulatory functions in known FGF21 activities such as the enhancement of the expression level of a glucose transporter, an increase in glucose uptake, a decrease in blood glucose level, and an increase in the amount of insulin synthesized.

The term "betaKlotho activity" is used in the present invention to mean the action possessed by betaKlotho, which is the action to allow FGF21 to coexist with an FGF receptor and to allow them to interact with each other, so as to activate a signaling system mediated by the FGF receptor; namely, "the function or activity to control the activity of FGF21 mediated by an FGF receptor" Likewise, the description "a protein having betaKlotho activity" is used to mean not only betaKlotho and a soluble partial protein thereof, but also "a protein having the function or activity of controlling the activity of FGF21 mediated by an FGF receptor."

Such betaKlotho has a typical anchor protein structure, in which a long extracellular domain associated with betaKlotho activity is ligated to a short intracellular domain via a transmembrane domain. Soluble betaKlotho only consisting of such extracellular domain also functions as "a protein having betaKlotho activity." Even if it is a short partial sequence, if it has betaKlotho activity, it can be used as a protein having betaKlotho activity in the present invention.

In the present specification, typical examples of a protein having betaKlotho activity include typical betaKlotho proteins such as a mouse full-length betaKlotho protein having the amino acid sequence shown in SEQ ID NO: 2, a soluble betaKlotho protein thereof having the amino acid sequence shown in SEQ ID NO: 3, a human betaKlotho protein having the amino acid sequence shown in SEQ ID NO: 8, and a soluble human betaKlotho protein thereof having the amino acid sequence shown in SEQ ID NO: 9. These amino acid sequences may comprise a mutation (a deletion, substitution, addition, or the like) of one or several amino acids. In addition, a Flag tag sequence (SEQ ID NO: 4), a V5 tag sequence (SEQ ID NO: 5), a His tag sequence (SEQ ID NO: 6) or a combination sequence thereof may be added to the carboxy terminus thereof. Moreover, such mouse betaKlotho protein has homology of 78% at the amino acid sequence level with such human betaKlotho protein, and the human betaKlotho protein has functions equivalent to those of the mouse betaKlotho protein. Accordingly, it can be anticipated that betaKlotho derived from organism species that is evolutionarily present in a distance such as the distance between a mouse and a human will have the same level of betaKlotho activity. Therefore, the betaKlotho protein of the present invention includes not only mouse- and human-derived betaKlotho proteins, but also proteins derived from other organism species having amino acid sequence homology of 78% or more, preferably 85% or more, and more preferably 90% or more with the amino acid sequence shown in SEQ ID NO: 2 or 8. Specifically, "a protein consisting of the amino acid sequence shown in any one of SEQ ID NO: 2, 3, 8, and 9, or a partial fragment thereof," "a protein consisting of an amino acid sequence comprising a deletion, substitution, or addition of one or several amino acids with respect to the amino acid sequence shown in any one of SEQ ID NO: 2, 3, 8, and 9," and "a protein consisting of an amino acid sequence having homology of 78% or more with the amino acid sequence shown in any one of SEQ ID NO: 2, 3, 8, and 9", which all have betaKlotho activity, correspond to the "betaKlotho proteins" of the present invention. It is to be noted that the term "homology" is used in the present invention to mean a converted numerical value indicating the "identity" in the calculation method of Lipman-Pearson (Lipman and Pearson, 1985; Science 227, 1435-1441).

Typical examples of DNA encoding such protein having betaKlotho activity include a mouse-derived betaKlotho gene (SEQ ID NO: 1) and a human-derived betaKlotho gene (SEQ ID NO: 7). However, known betaKlotho genes derived from other organism species may also be used. Even an unknown betaKlotho gene may be obtained from a DNA library derived from each organism species by a PCR method or a hybridization method using a probe or a primer designed based on the nucleotide sequence of DNA encoding mouse- or human-derived betaKlotho (wherein a mouse-derived nucleotide sequence is shown in SEQ ID NO: 1).

Mutant DNA obtained by applying site-directed mutagenesis or random mutagenesis to the DNA encoding a protein having betaKlotho activity may be used. Moreover, the partial sequence of each soluble fragment or the like may also be used as such "DNA encoding a protein having betaKlotho activity."

Specific examples of such "DNA encoding a protein having betaKlotho activity" include: DNA consisting of the nucleotide sequence shown in SEQ ID NO: 1 or 7, or DNA consisting of the partial fragment thereof," "DNA hybridizing under stringent conditions with DNA consisting of a sequence complementary to SEQ ID NO: 1 or 7," and "DNA encoding the amino acid sequence shown in any one of SEQ ID NOS: 2, 3, 8, and 9," which all "encode a protein having betaKlotho activity."

The aforementioned description "under stringent conditions" is used to mean highly restricted conditions. For example, such conditions consist of 2×SSC, 1×Denhardt's solution, and approximately 60° C.

With the use of such recombinant DNA comprising DNA encoding a betaKlotho protein, a betaKlotho protein can be obtained as an expression product from a transformed mammalian cell host system or the like, according to an ordinary method. The "recombinant DNA" itself can be used as an agent for controlling the activity of FGF21. However, the term "recombinant DNA" is used herein to mean that such recombinant DNA is operably linked to a promoter or the like used for the expression of the DNA in a transformed host. Thus, the recombinant DNA is typically comprised in an expression vector that can be administered to mammals including a human, such as retrovirus.

Both a native betaKlotho protein and a recombinant protein produced from mammalian cells transformed with an expression vector containing a betaKlotho gene may be purified, as necessary, by a publicly known protein purification method such as ultrafiltration, gel filtration, affinity chromatography, or a combined method thereof, and the thus purified protein may be then used.

Hereinafter, in the present invention, various types of proteins having betaKlotho activity, or equivalent products such as a partial fragment thereof having betaKlotho activity or a mutant thereof, are simply referred to as "betaKlotho" or "betaKlotho proteins" at times. Moreover, DNA encoding such protein having betaKlotho activity is simply referred to as "DNA encoding betaKlotho" or "a betaKlotho gene" at times.

[2] Concerning FGF21 Activity Specifically Detected in Adipocytes

1. Concerning FGF21

FGF21 is a substance that was discovered by PCR using primers designed based on the sequence of FGF19 (Non-Patent Document 9). It has been reported that FGF21 has the activity of allowing adipocytes to increasingly express a glucose transporter and the activity of promoting insulin synthesis in the islets of Langerhans (Non-Patent Documents 1 and 6). It has been confirmed that FGF21 activates FGFR1 and FGFR2 on the surface of an adipocyte (Non-Patent Document 1). Thus, it can be understood that the signals of such activities are transduced into cells via an FGF receptor and the aforementioned phenomena then take place.

The description "the activity of FGF21 mediated by an FGF receptor" or "the biological activity of FGF21 mediated by an FGF receptor" is used in the present invention to mean the activity occurring in a cell mediated by an FGF receptor, and in particular, mediated by FGFR1c or FGFR3c. For example, such activity indicates the activity of increasing the expression of a glucose transporter (GLUT) in an adipocyte.

In addition, as FGF21 used in the present invention, mammal-derived FGF21 such as human-derived FGF21 (for example, please refer to GenBank accession No. AB021975) is preferable. However, examples of FGF21 are not limited thereto. Not only native proteins but also recombinant FGF21 may be applied. Furthermore, if a certain protein has the aforementioned FGF21 activity, a part of the amino acid sequence thereof may be modified. In order to produce recombinant FGF21, an ordinary transformed host/vector system such as *Escherichia coli* or mammalian cells may be used, as appropriate.

2. Measurement of FGF21 Activity Mediated by Fgf Receptor

In general, each FGF binds to an FGF receptor on the surface of a cell to activate the FGF receptor, and it activates various types of signaling mechanisms in the cell, so that the FGF may act or function on the cell in a certain way. Thus, the observed action or function can be measured as the activity of the FGF.

A commonly used measurement method is a cell growth stimulating activity measurement method described in Ornitz, D. M., Xu, J., Colvin, J. S., McEwen, D. G., MacArthur, C. A., Coulier, F., Gao, G. and Goldfarb, M. (1996) Receptor specificity of the fibroblast growth factor family. J Biol Chem, 271, 15292-15297. The summary thereof is as follows. FGF used as a measurement target is added to a culture solution containing a cultured cell having an FGF receptor on the surface thereof, and the obtained mixture is cultured for a certain period of time. Thereafter, a labeled thymidine is added to the culture solution, followed by further culture for a certain period of time. By measuring the amount of the labeled thymidine incorporated into polymeric DNA during the culture, the degree of FGF to activate DNA synthesis is evaluated. (In the present invention as well, this method was adopted when the activity of FGF21 was measured in Examples 4, 5, 6, 8, 9, and 10.)

As stated above, FGF21 has the activity of increasing the expression of a glucose transporter (GLUT) in a cell, mediated by an FGF receptor, and particularly mediated by FGFR1c on the cell surface. Hence, with regard to the analysis of the FGF21 activity of the present invention, in Example 1, the typical activity of FGF21 to increase the expression of GLUT in a test cell was measured in terms of the expression level of GLUT1 mRNA.

Herein, FGF21 is added in various types of concentrations to a cell culture solution, so as to allow the FGF21 to act on the cell, and the mixture is then cultured for a certain period of time. Thereafter, mRNA is extracted from the cell, and the expression level of GLUT1 mRNA is then measured. If the expression level of such mRNA is increased, it is determined that FGF21 exhibits its activity.

For the purpose of analyzing an increase in the expression of GLUT1, it may also be possible to measure the expression level of a GLUT1 protein by a known method such as a Western blot method using a GLUT1 antibody or the like. In addition, in the case of an experimental animal and the like, by producing a transgenic animal, into which a control region for controlling the transcription of GLUT1 (for example, a promoter region) and a reporter gene ligated downstream thereof such that transcription can be controlled have been incorporated, FGF21 activity may also be measured by measuring the expression level of the reporter gene.

Methods for measuring FGF21 activity are not limited thereto. Any method can be applied, as long as it enables quantitative measurement. For example, there may also be applied a method, which comprises measuring the activation of an FGF receptor or the activation of a signaling molecule located downstream thereof in terms of an increase in the phosphorylated level of the FGF receptor or the signaling molecule, and then evaluating it.

In a preferred embodiment of the measurement of the expression level of GLUT1 mRNA for the measurement of FGF21 of the present invention, a cultured adipocyte can be used as a test cell.

As such cultured adipocytes, various types of cultured adipocytes such as human or rat primary cultured cells can be used. In the embodiments of the present invention, there were applied 3T3-L1 cells, which have been widely used in the present study field as fibroblasts having the ability to differentiate into adipocytes as a result of the control of culture conditions. Such 3T3-L1 cells have characteristics as fibroblasts before induction of differentiation, and have characteristics as adipocytes after induction of differentiation. Thus, the effects obtained by allowing FGF21 to act on the cells can be analyzed by comparing the two above cases. The description "cells having characteristics as adipocytes" is herein used to mean cells, which conduct intracellular metabolism specific to adipocytes and have cytoplasm in which large quantities of fat droplets are accumulated. An experimental system for inducing 3T3-L1 cells to adipocytes is disclosed, for example, in Kharitonenkov, A., Shiyanova, T. L., Koester, A., Ford, A. M., Micanovic, R., Galbreath, E. J., Sandusky, G. E., Hammond, L. J., Moyers, J. S., Owens, R. A., Gromada, J., Brozinick, J. T., Hawkins, E. D., Wroblewski, V. J., Li, D. S., Mehrbod, F., Jaskunas, S. R., and Shanafelt, A. B. (2005) J Clin Invest 115(6), 1627-1635.

3. Specific detection of increase in expression level of GLUT in adipocytes, Caused by Action of FGF21

3T3-L1 cells were induced to differentiate into adipocytes. Both cells having characteristics as adipocytes after the differentiation induction and cells having characteristics as fibroblasts before the differentiation induction were prepared. FGF21 in various types of concentrations was allowed to act on the cells, and in each concentration of FGF21, the expression level of GLUT1 mRNA was measured. The results of the two types of cells were compared with each other. In the case of cells differentiating into adipocytes, the expression level of GLUT1 mRNA was increased, as the concentration of FGF21 was increased. These results demonstrated that FGF21 exhibits its activity on adipocytes and increases the expression of GLUT1. In contrast, in the case of fibroblasts that had not differentiated into adipocytes, even if the concentration of FGF21 was changed, the expression level of GLUT1 mRNA was hardly changed. These results demonstrated that the activity of FGF21 to increase the expression level of GLUT1 is specifically detected in a case in which 3T3-L1 cells have differentiated into adipocytes.

[3] Detection of Fluctuation in Expression of FGF Receptor Associated with Differentiation into Adipocytes 1. Concerning FGF Receptor FGF receptor (FGFR) is a single-pass transmembrane protein existing on the surface of a cell. At present, 5 types of FGF receptors, namely, FGFR1 to 5 were identified. Of these, FGFR1 to 4 are tyrosine kinase-type receptors, and when FGF binds to such receptor, it becomes activated as a result of dimerization or autophosphorylation. The activated FGFR interacts with a signaling molecule in a cell, so that it activates multiple signaling pathways. As a result of selective splicing, FGFR1 to 3 have mainly two types of isoforms (FGFR1b, FGFR1c, FGFR2b, FGFR2c, FGFR3b, and FGFR3c).

2. Fluctuation in Expression Level of FGF Receptor Associated with Differentiation into Adipocytes There was a possibility that the results in [1]3 above might be obtained as a result of an increase in the amount of signaling in a cell due to the expression of an FGF receptor on the cell surface or an increase in such expression level associated with differentiation of 3T3-L1 cells into adipocytes. Thus, the expression level of each FGF receptor was measured at each stage of induction of differentiation of 3T3-L1 cells into adipocytes.

By controlling the culture conditions of 3T3-L1 cells, cells having characteristics as fibroblasts were gradually induced to differentiate into cells having characteristics as adipocytes. At each stage, total RNA was extracted from the cells, and the expression level of FGF receptor mRNA at the stage was then measured, so as to detect a fluctuation in the expression of the FGF receptor associated with differentiation into adipocytes.

As a result, regardless of the presence or absence of differentiation into adipocytes, FGFR1 and FGFR2 were expressed at high levels. In contrast, the expression level of FGFR3 and that of FGFR4 were extremely low. There were no receptors whose expression was increased associated with differentiation. In both FGFR1 and FGFR2, which were expressed at high levels, the expression level tended to be slightly decreased associated with differentiation.

[4] Detection of Fluctuation in Expression of BetaKlotho Associated with Differentiation into Adipocytes The present inventors have thought that, if there is a substance whose expression level on the surface of an adipocyte is increased during the process of differentiation into an adipocyte, the substance is highly likely to act on an FGF receptor in cooperation with FGF21. The inventors have focused attention on betaKlotho known to be expressed in the adipose tissues of a developing mouse fetus (Non-Patent Document 8 and Patent Document 1), and they have examined a change in the expression level of betaKlotho associated with differentiation of a 3T3-L1 cell into an adipocyte.

Specifically, 3T3-L1 cells were gradually induced to differentiate into adipocytes by the same method as that described in [2]3 above. At each stage, total RNA was extracted from the cells, and the expression level of betaKlotho mRNA at the stage was then measured, so as to detect a fluctuation in the expression of betaKlotho associated with differentiation into adipocytes.

As a control, a fluctuation in the expression level of another gene differing from betaKlotho can be detected. Thus, such another gene is preferable. In the embodiment of the present invention, a fluctuation in the expression of a Klotho gene having homology of 41% at the amino acid sequence level with betaKlotho was adopted as a control. By comparing betaKlotho with such Klotho, it is found that there is a significant increase in the expression of betaKlotho associated with induction to adipocytes.

These results suggest that an increase in the expression of betaKlotho associated with induction to adipocytes is closely related to the functions of the adipocytes.

[5] Analysis of Necessity of BetaKlotho in Realization of FGF21 Activity

1. Association of Realization of FGF21 Activity Mediated by FGF Receptor with BetaKlotho From the results of the aforementioned experiment using 3T3-L1 cells and adipocytes induced to differentiate from the 3T3-L1 cells, it is suggested that the activity of FGF21 specific to adipocytes is induced in a case in which both an FGF receptor and betaKlotho exist. That is to say, it is strongly suggested that, when 3T3-L1 cells are induced to differentiate into adipocytes, together with an FGF receptor originally existing on the surface thereof, such as FGFR1c, betaKlotho may be expressed, and that this betaKlotho may significantly increase the activity of FGF21 mediated by the FGF receptor.

In order to confirm the correctness of this suggestion, in the embodiment of the present invention, whether or not FGF21 has activity on a cell which has expressed only the FGF receptor, and on a cell which has expressed both the FGF receptor and betaKlotho, is analyzed. For this purpose, it is necessary to use a cell that has originally expressed neither the FGF receptor nor betaKlotho.

2. Method for Producing Test Cell that Expresses FGF Receptor and/or BetaKlotho

As a cell that has originally expressed neither an FGF receptor nor betaKlotho, which is suitable for the aforementioned purpose, a BaF3 cell that is a mouse leukemia ProB cell can be used. However, other types of cells may also be used, as long as they have not expressed any of these genes on the surface thereof, but are able to express such genes on the surface thereof when they are transformed with the genes. A cell, which has originally expressed these genes, may also be used, if the genes are actually knocked out.

A cell that had expressed neither the FGF receptor nor betaKlotho was used as a host. A BaF3 cell, which had expressed only an FGF receptor gene or only a betaKlotho gene on the surface thereof, was prepared by a common genetic recombination technique. At the same time, using the two types of genes, the same method was applied to produce a BaF3 cell, which has expressed a different type of FGF receptor as well as betaKlotho on the surface thereof.

A method for producing such expressing cell is not particularly limited. For instance, an expression plasmid is introduced into cells using a lipofectamine reagent, and a drug resistance gene on the plasmid is used as a marker, so as to obtain a cell line resistant to the drug.

3. Analysis of Necessity of BetaKlotho for Provocation of Signal Downstream of FGF Receptor by FGF21

BaF3 cells were transformed with both FGFR1c cDNA and betaKlotho cDNA, so as to obtain multiple clones. Thereafter, confirmation was carried out using a betaKlotho antibody on SDS-PAGE gel. As a result, a broad smear band, which is characteristic for the modification of an N-type sugar chain, was observed. From these results, betaKlotho is considered to be a glycoprotein having a modified N-type sugar chain.

Moreover, it was demonstrated that, when FGF21 is added to a culture solution, a cell that has expressed FGFR1c but has not expressed betaKlotho does not react with the FGF21, regardless of the presence or absence of heparin, and that only a cell that has expressed betaKlotho as well as FGFR1c reacts with the FGF21.

Furthermore, from the results of an experiment in which heparin was allowed to act on a BaF3 cell that had expressed both FGFR1c and betaKlotho, while changing the amount of FGF21, it was found that heparin increases the action of FGF21. However, a BaF3 cell that has not expressed FGFR1c but has expressed only betaKlotho is not reactive with FGF21, regardless of the presence or absence of heparin.

The aforementioned results demonstrated that both an FGF receptor and betaKlotho are necessary for heparin to react with FGF21, and that heparin or a heparin-like substance (a substance that increases FGF activity mediated by an ordinary FGF receptor) has the effect of further increasing the activity of a protein having betaKlotho activity to increase FGF21.

This means that whether or not a test substance has the action to increase or suppress the activity of FGF21 can be detected by allowing the test substance to exist in a BaF3 cell system that has expressed FGFR1c, and by allowing FGF21 to act on the system. If a test substance is allowed to exist in a BaF3 cell system that has expressed betaKlotho as well as FGFR1c, and if FGF21 is allowed to act on the system, whether or not the test substance has the action to further increase or suppress the activity of betaKlotho to increase FGF21 can be detected. That is to say, it is shown that a BaF3 cell system that has expressed an FGF receptor is preferably used to screen for a substance that increases or suppresses the activity of FGF21, and that a BaF3 cell system that has expressed betaKlotho as well as an FGF receptor is preferably used to screen for a substance that increases or suppresses the activity of betaKlotho to control the FGF21 activity. Further, a BaF3 cell system that has expressed betaKlotho as well as an FGF receptor can also be used to screen for an FGF21-like active substance.

All of substances obtained by these screening methods can be used as agents for controlling the activity of FGF21 which is exhibited in the coexistence of an FGF receptor and betaKlotho, and pharmaceutical compositions for controlling the FGF21 activity, such as a pharmaceutical composition for controlling blood glucose level.

[6] Analysis of Specificity of FGF Receptor Existing with BetaKlotho in Realization of FGF21 Activity From the above experimental results, it was clarified that the coexistence of FGF21 and betaKlotho is able to activate FGFR1c as an FGF receptor, thereby transmitting a signal into a cell that has expressed it. In order to examine such betaKlotho-coexisting effect in the case of other FGF receptors, there was produced a BaF3 cell, which had expressed a different type of an FGF receptor and betaKlotho. The activity of FGF21 on the cell was then evaluated. As a result, it became clear that, when not only FGFR1c but also FGFR3c is allowed to express together with betaKlotho, it reacts with FGF21. In such a case also, reactivity is further increased by the presence of heparin.

Accordingly, heparin has the action to further increase the effect of betaKlotho to increase the activity of FGF21 mediated by an FGF receptor.

In addition, in the case of the BaF3 cell system used herein, which has expressed betaKlotho as well as an FGF receptor, FGF21 may be allowed to act on the cell system in a state in which the FGF receptor and betaKlotho coexist on the cell surface. Thus, this cell system can be used in screening for a substance that enhances or suppresses a signaling system mediated by the FGF receptor, which is exhibited in the coexistence of FGF21, betaKlotho, and the FGF receptor.

The substance obtained by the aforementioned screening can be used as a pharmaceutical composition (for example, a pharmaceutical composition for controlling blood glucose level) or the like used for enhancing or suppressing a signaling system mediated by the FGF receptor, which is exhibited in the coexistence of FGF21, betaKlotho, and the FGF receptor. That is to say, since it can be said that heparin is a substance obtained by the aforementioned screening system as a substance that increases the effect of betaKlotho to increase the activity of FGF21 mediated by an FGF receptor. Accordingly, as a specific example, heparin can be used as an active ingredient contained in the aforementioned pharmaceutical composition.

[7] Confirmation of BetaKlotho as a Co-Receptor Specific to FGF21 in Binding to FGF Receptor According to the present invention, if FGF21 coexists with betaKlotho, they are able to activate an FGF receptor and transmit a signal into a cell. Next, whether such FGF21 and betaKlotho are specific to each other, or the relationship between such FGF21 and betaKlotho is flexible to such an extent that a substance having structural similarity to such FGF21 or betaKlotho can be replaced with them, was examined. That is, as a specific experiment, betaKlotho was allowed to act on FGF23 having high structural similarity to FGF21, and Klotho having high structural similarity to betaKlotho was allowed to act on FGF21. The level of compatibility was then examined in each case.

As a result, in the case of FGF21, even if Klotho existed, it did not react with FGFR1c, regardless of the presence or absence of heparin. On the contrary, in the case of FGF23, even if betaKlotho existed, it did not react with FGFR1c, regardless of the presence or absence of heparin. In addition, in both cases, if heparin existed in the system, the reactivity with FGFR1c was increased.

Accordingly, it was demonstrated that betaKlotho is a co-receptor specific to FGF21 in binding to FGF receptor. At the same time, it was also demonstrated that heparin is an effective factor for increasing such effect.

[8] Use of BetaKlotho and Substance that Enhances or Suppresses BetaKlotho Activity Summing up the aforementioned results, it was demonstrated that a protein having betaKlotho activity or a betaKlotho gene capable of expressing in vivo such protein having betaKlotho activity can be used as an agent for controlling FGF21 activity, and that betaKlotho or a gene thereof can be used as a pharmaceutical composition for controlling blood glucose level, which comprises it as an active ingredient, singly or in combination with FGF21.

Moreover, when a cell or tissue that has originally expressed betaKlotho is used as a target, it may also be effective to use a substance that increases the betaKlotho activity and/or a substance that promotes the expression of the betaKlotho. It may also be possible to use such substance together with a betaKlotho protein or a betaKlotho gene.

On the contrary, a substance that inhibits betaKlotho activity in vivo acts as an agent for suppressing the activity of FGF21 mediated by an FGF receptor. Thus, it can be anticipated that such substance will suppress the function of FGF21 to decrease blood glucose level, which is a typical activity of FGF21, and will have the effect of increasing blood glucose level, for example.

An example of a substance that enhances betaKlotho activity in vivo is heparin, which was confirmed to have such property in the example section. However, the type of such substance is not particularly limited, as long as it increases the action of betaKlotho in vivo. The substance that enhances betaKlotho activity can be easily obtained by the screening method of the present invention using a BaF3 cell or the like, which has expressed betaKlotho and an FGF receptor on the surface thereof. An example of a candidate substance is, what is called, an agonistic antibody imitating betaKlotho activity, among anti-betaKlotho antibodies. Such antibody may include, not only an antibody recognizing betaKlotho, but also an antibody recognizing an FGF receptor, an antibody recognizing FGF21, and an antibody recognizing a complex of an FGF receptor and/or FGF21.

Examples of an agonistic antibody against the action of a growth factor include an agonistic antibody to the HGF receptor (Patent Document 2), a Tie2 agonistic antibody (Patent Document 3), an agonistic antibody to the EGF receptor (Non-Patent Document 10), and an agonistic antibody to the NGF receptor (Non-Patent Document 11).

By the way, in the case of many FGF ligands such as FGF1, the activation of an FGF receptor does not occur only when a single FGF ligand binds to the FGF receptor. However, if a heparin-like sugar chain coexists therewith, an active complex is formed, and signaling then takes place using such active complex as an origin, so that cell response (for example, cell growth or the like) may occur ((1) and (2) in the lower case of FIG. 14). In the activation of FGF21 mediated by an FGF receptor in the present invention, signaling does not occur in an ordinary manner between an FGF receptor and an FGF ligand, as described in (1) and (2). The activation of the FGF receptor due to FGF21 takes place for the first time, when a co-receptor betaKlotho is added and three components, a ligand (FGF21), an FGF receptor, and betaKlotho exist. This phenomenon is shown as a conceptual view in (3) in the lower case of FIG. 14. The number of molecules associated with the formation of a complex in the conceptual view is not limited. A substance that increases or decreases the formation of this active complex has the action to enhance or suppress the action of FGF21. Such substance can be easily obtained by the screening system using the cell system of the present invention for expressing betaKlotho and an FGF receptor, and it can be used as an agent or a pharmaceutical composition for controlling the activity of FGF21 (4).

Figure 14:
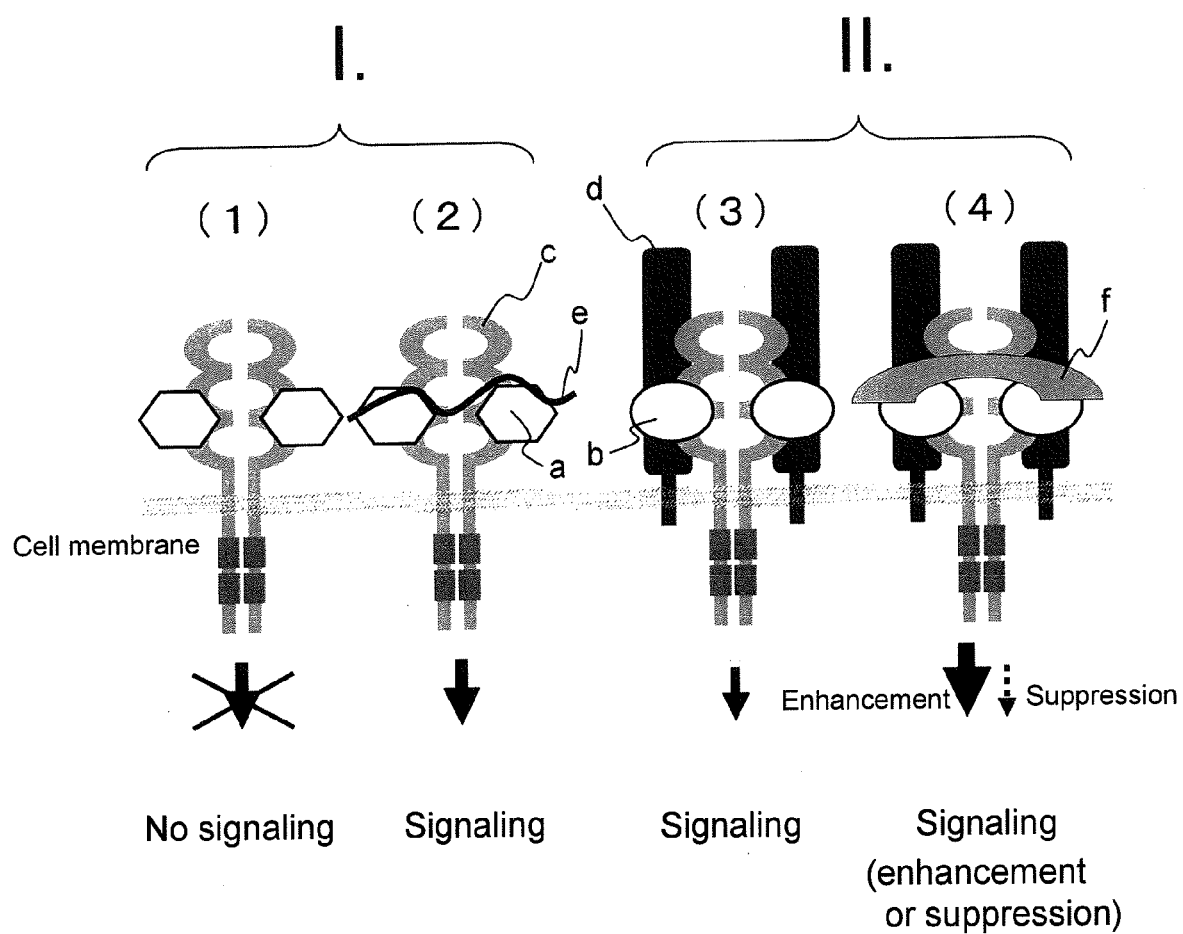
FIG. 14 is a conceptual view showing the present invention. In the figure, the letter a indicates many types of FGF members such as FGF1 and FGF2, the letter b indicates FGF21, the letter c indicates an FGF receptor, the letter d indicates betaKlotho, and the letter e indicates heparin or a heparin-like sugar chain. In addition, a substance (group) that increases or decreases the formation of an active complex among FGF21, an FGF receptor, and betaKlotho is indicated by the letter f. I. The action mechanism of many FGF members such as FGF1 to activate an FGF receptor in the absence of betaKlotho, which has been known from previous studies: (1) the activation of such FGF receptor does not occur even when a single FGF ligand binds to such FGF receptor; and (2) if a heparin-like sugar chain coexists therewith, an active complex capable of provoking a signal is formed, signaling takes place using such active complex as an origin, so that cell response (for example, cell growth) occurs. II. The action mechanism of FGF21 to activate an FGF receptor in the existence of betaKlotho, which has been discovered in the present invention: (3) a co-receptor betaKlotho is added, and thereby, three factors, namely, a ligand (FGF21), an FGF receptor, and betaKlotho exist, and as a result, the activation of the FGF receptor by FGF21 takes place; and (4) a substance that increases or decreases the formation of an active complex capable of provoking such signal has the action to enhance or suppress the action of FGF21.

The conventional agonistic antibody has the action to promote the binding of a ligand to a receptor on the surface of a cell. An antibody imitating betaKlotho activity in the present invention also increases the formation of a complex consisting of betaKlotho, FGF21, and an FGF receptor, as shown in FIG. 14(4). As a result, it is considered that this antibody has the action to enhance the activity of FGF21 mediated by an FGF receptor.

The type of a substance that suppresses betaKlotho activity in vivo is not particularly limited, as long as it is a substance that inhibits the action of betaKlotho in vivo. A typical example is a betaKlotho-specific antibody.

Both an agonistic antibody imitating betaKlotho activity and a betaKlotho-specific antibody suppressing betaKlotho activity (hereinafter simply referred to as a "betaKlotho antibody" at times) may be either a polyclonal antibody or a monoclonal antibody. Such antibody may be produced by a publicly known immunological method. Moreover, such betaKlotho antibody may also be an antibody fragment (for example, Fab and $F(ab')_2$) or a recombinant antibody (for example, a single stranded antibody). Furthermore, a nucleic acid encoding an antibody that suppresses betaKlotho activity (which is operably linked to a nucleic acid having promoter activity) is preferable as a substance that suppresses the expression of betaKlotho.

For example, a polyclonal antibody can be obtained by immunizing a mammal such as a rat, a mouse, or a rabbit with betaKlotho or a fragment thereof, together with a commercially available adjuvant, according to an ordinary method, using a carrier protein, as necessary, and then purifying the obtained antiserum.

On the other hand, a monoclonal antibody can be obtained by a cell fusion method. For example, a mouse or the like is immunized with betaKlotho or a fragment thereof, and thereafter, leukocyte was collected from the spleen or lymph node. The leukocyte was fused with a myeloma cell to obtain a hybridoma for producing an anti-betaKlotho monoclonal antibody.

Further, the antibody of the present invention may be any one of a chimeric antibody, a humanized antibody, and a human antibody. The chimeric antibody can be produced with reference to "*Jikken Igaku* (Experimental Medicine), Suppl., Vol. 6, No. 10, 1988, and the like. The humanized antibody can be produced with reference to JP Patent Publication (Kohyo) No. 4-506458 A (1992), JP Patent Publication (Kokai) No. 62-296890 A (1987), and the like. The human antibody can be produced with reference to Nature Genetics, Vol. 15, pp. 146-156, 1997, Nature Genetics, Vol. 7, pp. 13-21, 1994, and the like.

Other betaKlotho inhibitory substances include an antisense nucleic acid of a betaKlotho gene, ribozyme, RNAi-inducible nucleic acid, a targeting vector, and a partial negative mutant of betaKlotho.

Still further, a simple betaKlotho inhibitory substance can also be screened by the screening method described in Patent Document 1.

[9] Concerning Pharmaceutical Composition Associated with Control (Increasing or Decreasing Action) of Blood Glucose Level of the Present Invention The agent of the present invention may comprise any given carriers, for example, a pharmaceutically acceptable carrier, as well as betaKlotho and an agent for controlling the expression or function thereof. Examples of such pharmaceutically acceptable carrier include: excipients such as sucrose, starch, mannite, sorbit, lactose, glucose, cellulose, talc, calcium phosphate, or calcium carbonate; binders such as cellulose, methylcellulose, hydroxypropylcellulose, polypropylpyrrolidone, gelatin, gum arabic, polyethylene glycol, sucrose, or starch; disintegrators such as starch, carboxymethylcellulose, hydroxypropyl starch, sodium-glycol-starch, sodium bicarbonate, calcium phosphate, or calcium citrate; lubricants such as magnesium stearate, Aerogil, talc, or sodium lauryl sulfate; aromatics such as citric acid, menthol, glycyrrhizin ammonium salt, glycine, or orange powder; preservatives such as sodium benzoate, sodium hydrogen sulfite, methylparaben, or propylparaben; stabilizers such as citric acid, sodium citrate, or acetic acid; suspending agents such as methylcellulose, polyvinyl pyrrolidone, or aluminum stearate; dispersants such as a surfactant; diluents such as water, normal saline, or orange juice; base waxes such as cacao butter, polyethylene glycol, or white kerosine. However, examples are not limited thereto.

Pharmaceutical agents preferable for oral administration include: a liquid agent produced by dissolving an effective dose of substance in a diluent such as water or a normal saline; a capsule agent comprising an effective dose of substance in the form of a solid or a granule; a sachet or a tablet; a suspension agent produced by suspending an effective dose of substance in a suitable dispersion medium; and an emulsion produced by dispersing and emulsifying in a suitable dispersion medium a solution in which an effective dose of substance has been dissolved.

Pharmaceutical agents preferable for parenteral administration (for example, intravenous injection, hypodermic injection, intramuscular injection, local injection, etc.) include aqueous and nonaqueous, isotonic, aseptic injection agents. Such injection agent may comprise an antioxidant, a buffer, a disinfecting agent, an isotonizing agent, and the like. In addition, other examples of the aforementioned pharmaceutical agents include aqueous and nonaqueous, aseptic suspension agents. Such suspension agent may comprise a suspending agent, a solubilizer, a thickener, a stabilizer, an antiseptic agent. This pharmaceutical agent may be encapsulated in a container such as an ampule or a vial, at a unit dose or at doses over several administrations. Otherwise, if an active ingredient and a pharmaceutically acceptable carrier are freeze-dried and the thus freeze-dried product is dissolved or suspended in a suitable aseptic vehicle immediately before use, it can be preserved in a good condition.

The dosage of the agent of the present invention differs depending on the activity or type of an active ingredient, the degree of severity of disease, animal species as an administration target, the body weight, age, and agent acceptability of the administration target, and the like. Thus, it all depends. In general, the effective amount of active ingredient is approximately 0.001 to approximately 500 mg/kg per adult per day.

In addition, when the agent of the present invention comprises, as an active ingredient, recombinant DNA containing DNA encoding betaKlotho, the present agent typically comprises, as an active ingredient, an expression vector into which DNA encoding betaKlotho used as such recombinant DNA has been inserted. In such expression vector, an oligonucleotide or polynucleotide encoding the aforementioned nucleic acid molecule must be operably linked to a promoter capable of exhibiting its promoter activity in a mammalian cell as an administration target. The type of a promoter used herein is not particularly limited, as long as it is able to function in a mammal used as an administration target. An example of such promoter is an SV40-derived early promoter. Such promoter is preferably administered together with a virus vector suitable as an expression vector used for administration to mammals including a human, such as adenovirus, retrovirus, adeno-associated virus or herpes virus, or a nucleic acid carrier substance.

[10] Screening Method and Kit Using Cell System that has Endogenously Expressed Neither FGF Receptor nor BetaKlotho As a cell that has endogenously expressed neither an FGF receptor nor betaKlotho, a BaF3 cell, which is a mouse leukemia ProB cell, is typically used. Thus, explanation will be given below, using the BaF3 cell. However, other types of cells may also be used, as long as both genes are not expressed on the cell surface and such genes can be expressed on the cell surface if the cells are transformed with them. Thus, the type of available cell is not limited to the BaF3 cell.

A BaF3 cell system that has expressed an FGF receptor can be used to screen for a substance that increases or suppresses the activity of FGF21 mediated by the FGF receptor.

Specifically, first, there can be applied a method of allowing FGF21 as well as a test substance to act on a BaF3 cell culture system that has expressed an FGF receptor on the cell surface thereof. At that time, the order of adding a test substance and FGF21 is not limited. They may be simultaneously added, or either one may be added first.

Moreover, a test substance gene as well as an FGF receptor gene may be introduced into a BaF3 cell, and FGF21 may be then allowed to act on the BaF3 cell system that has expressed both the FGF receptor and the test substance on the surface thereof.

At that time, the test substance gene and the FGF receptor gene may be inserted into a single vector. Or, the two genes may also be inserted into each different vectors, and such vectors may be then introduced into the BaF3 cell simultaneously. Otherwise, the test substance gene may also be introduced into a BaF3 cell that has expressed an FGF receptor on the surface thereof.

As an FGF receptor and the gene thereof, FGFR1c or FGFR3c, and the gene thereof, are preferably used.

Accordingly, by combining FGF21 with a BaF3 cell system that has expressed an FGF receptor, and preferably FGFR1c or FGFR3c, on the surface thereof, there can be produced a kit for screening for a substance that increases or suppresses the biological activity of FGF21.

In actual screening, the growth ability of the BaF3 cell can be evaluated by comparing with a control system to which no test substance is added. The growth ability of the BaF3 cell is measured by an ordinary method such as the measurement of the uptake of labeled thymidine. The same applies to other screening methods.

Furthermore, in actual screening, the activation of BaF3 cell growth signaling can be evaluated by comparing with a control system to which no test substance is added. The activation of such BaF3 cell growth signaling is measured by an ordinary method such as tyrosine phosphorylation of an FGF receptor, tyrosine phosphorylation of FGF receptor substrate 2 (FRS2), or phosphorylation of MAP kinase (ERK1/2). The same applies to other screening methods.

A BaF3 cell system that has expressed betaKlotho as well as an FGF receptor can be used to screen for a substance that increases or suppresses betaKlotho activity having the action to control the activity of FGF21.

Specifically, first, there can be applied a method of allowing FGF21 as well as a test substance to act on a BaF3 cell system that has expressed an FGF receptor and betaKlotho on the cell surface thereof. At that time, the order of adding a test substance and FGF21 is not limited. They may be simultaneously added, or either one may be added first.

Moreover, a test substance gene as well as an FGF receptor gene and betaKlotho may be introduced into a BaF3 cell, and FGF21 may be then allowed to act on the BaF3 cell system that has expressed the test substance as well as the FGF receptor and betaKlotho on the surface thereof.

At that time, the test substance gene, the FGF receptor gene, and the betaKlotho gene may be inserted into a single vector. Or, the they may also be inserted into each different vectors, and such vectors may be then introduced into the BaF3 cell simultaneously. Otherwise, the test substance gene may also be introduced into a BaF3 cell that has expressed an FGF receptor and betaKlotho on the surface thereof.

As an FGF receptor and the gene thereof, FGFR1c or FGFR3c, and the gene thereof, are preferably used.

Accordingly, by combining FGF21 with a BaF3 cell system that has expressed an FGF receptor, preferably FGFR1c or FGFR3c, and betaKlotho on the surface thereof, there can be produced a kit for screening for a substance that enhances or inhibits the activity of betaKlotho associated to the action to control the activity of FGF21.

The BaF3 cell system that has expressed an FGF receptor and betaKlotho can be used in a method for screening for an FGF21-like active substance.

Specifically, a test substance is allowed to act on the BaF3 cell system that has expressed an FGF receptor and betaKlotho on the surface thereof, and the growth ability of the BaF3 cell is evaluated, thereby screening for an FGF21-like active substance.

During such screening, a test substance is allowed to simultaneously act on a BaF3 cell system that has expressed only an FGF receptor on the surface thereof and/or a BaF3 cell system that has expressed only betaKlotho on the surface thereof, so that it can preferably be confirmed that the action is based on a phenomenon whereby a complex of the FGF receptor and betaKlotho has been formed.

As such FGF receptor, FGFR1c or FGFR3c is preferably used.

Using the BaF3 cell system that has expressed an FGF receptor, preferably FGFR1c or FGFR3c, and betaKlotho on the surface thereof, a kit for screening for an FGF21-like active substance can be produced.

A kit, which further comprises, as a control system(s), a BaF3 cell system that has expressed only an FGF receptor on the surface thereof and/or a BaF3 cell system that has expressed only betaKlotho on the surface thereof, can more preferably be used.

Substances obtained by such screening kits can all be used as agents for controlling the activity of FGF21 exhibited in the coexistence of an FGF receptor and betaKlotho and as pharmaceutical compositions for controlling such FGF activity.

EXAMPLES

The present invention will be described more in detail below in the following examples. However, these examples are not intended to limit the technical scope of the present invention.

Example 1

Detection of Activity of FGF21 Specific to Adipocytes

It has been reported that FGF21 allows adipocytes to increasingly express glucose transporter 1 (GLUT1). In the present example, as cultured adipocytes, there were used 3T3-L1 cells that are fibroblasts having the ability to differentiate into adipocytes by controlling culture conditions. The cells were cultured in a culture solution of a Dulbecco's modified Eagle medium (DMEM) containing 10% fetal bovine serum (FBS), so as to prepare cells maintaining an undifferentiated property as fibroblasts. The prepared cells were cultured in a test system, and they were allowed to grow to a confluent state. The cells were then left for 2 days. Thereafter, the culture solution was exchanged with DMEM as a culture solution used for differentiation induction, which comprised 10% FBS, 0.25 µM dexamethasone, 0.5 mM methyl isobutyl xanthine, and 5 µg/ml insulin. The cells were cultured for 2 days. Thereafter, the culture solution was exchanged with DMEM comprising 10% FBS and 2.5 µg/ml insulin every two days. Thus, cells having the properties of inducibly differentiated adipocytes were obtained. For comparison, fibroblasts whose differentiation had not been induced were also prepared. The term "cells having the properties of adipocytes" is used herein to mean cells, which conduct intracellular metabolism specific to adipocytes and have cytoplasm in which large quantities of fat droplets are accumulated.

FGF21 were added in various types of concentrations to such different types of culture solutions, and the cells were further culture for 6 hours. Thereafter, RNA was extracted, and the copy number of GLUT1 was counted. The results are shown in FIG. 1.

Herein, in the case of cells that had differentiated into adipocytes, the expression level of GLUT1 mRNA was increased by adding FGF21 in various types of concentrations to cell culture solutions. These results demonstrated that FGF21 exhibits its activity on adipocytes, so as to increase the expression of GLUT1. In contrast, in the case of undifferentiated fibroblasts, even though FGF21 were added in various types of concentrations to such cell culture solutions, the expression level of GLUT1 mRNA was hardly changed. These results demonstrated that the activity of FGF21 to increase GLUT1 mRNA exhibits only after 3T3-L1 cells have differentiated into adipocytes.

Example 2

Detection of Fluctuation in Expression of FGF Receptor Associated with Differentiation of Adipocytes In the above Example 1, FGF21 exhibited its activity only after 3T3-L1 cells had differentiated into adipocytes. Thus, there was a possibility that, as a result of an increase in the number of FGF receptors existing on the cell surface associated with differentiation of the cells into adipocytes, reactivity with FGF21 increased. Hence, whether or not the expression level of an FGF receptor molecule is changed was first analyzed.

The culture solution containing 3T3-L1 cells was exchanged with a culture solution for differentiation induction. After initiation of the culture, the cells having the properties of fibroblasts were gradually converted over time to cells having the properties of adipocytes.

Figure 2:
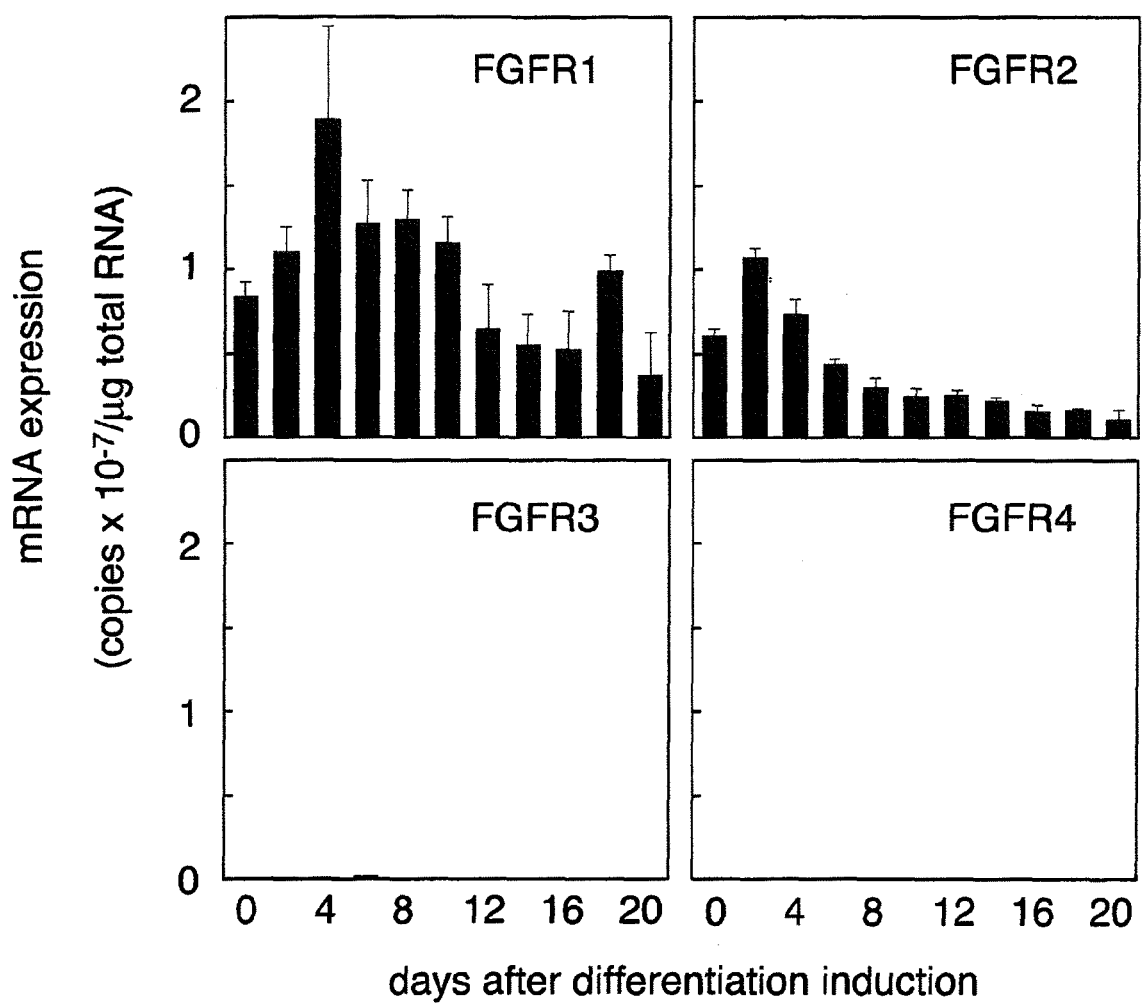
FIG. 2 is a characteristic figure showing the detection results of a fluctuation in FGF receptor expression associated with differentiation into adipocytes. In the figure, the horizontal axis indicates the number of days after induction of differentiation from fibroblasts into adipocytes, and the longitudinal axis indicates the expression level of FGF receptor mRNA. FGFR1 and FGFR2 were expressed at high levels. In contrast, the expression level of FGFR3 and that of FGFR4 were extremely low. Both the expression level of FGFR1 and that of FGFR2 tended to be slightly decreased with differentiation.

Thus, a differentiation induction treatment was carried out under the same conditions as those of Example 1. Thereafter, 3T3-L1 cells were collected every two days for 20 days, and the expression level of FGF receptor mRNA expressed by the cells was analyzed. With regard to such FGF receptors, 4 types of genes, FGFR1, FGFR2, FGFR3, and FGFR4 have been known as single-pass transmembrane tyrosine kinase receptors. The expression level of mRNA in such gene was measured. The results are shown in FIG. 2. Regardless of the presence or absence of differentiation, FGFR1 and FGFR2 were expressed at high levels, and the expression level of FGFR3 and that of FGFR4 were extremely low. There were no receptors whose expression was increased associated with differentiation. Rather, the expression levels of both the FGFR1 and FGFR2 receptors, which were expressed at high levels, tended to be slightly decreased with differentiation.

Example 3

Detection of Fluctuation in Expression of BetaKlotho Associated with Differentiation of Adipocytes The present inventors have considered that, if there is a substance whose expression level on the surface of an adipocyte is increased during the process of cell differentiation into the adipocyte, such substance is highly likely to act on an FGF receptor in cooperation with FGF21. The inventors have focused on betaKlotho that had been known to be expressed in the adipose tissue of a developing mouse fetus.

The expression level of betaKlotho was analyzed over time in the process of differentiation of a 3T3-L1 cell into an adipocyte in the same manner as that described above in Example 2.

Furthermore, for comparison, the expression level of Klotho, which had been currently reported to act as a co-receptor on FGF23, was also analyzed. Klotho is structurally similar to betaKlotho, and it shows homology of 41% at the amino acid sequence level with betaKlotho (55% at the nucleotide sequence level). The properties of Klotho are completely different from those of betaKlotho. Thus, they are considered to be molecules encoded by clearly different genes.

Figure 3:
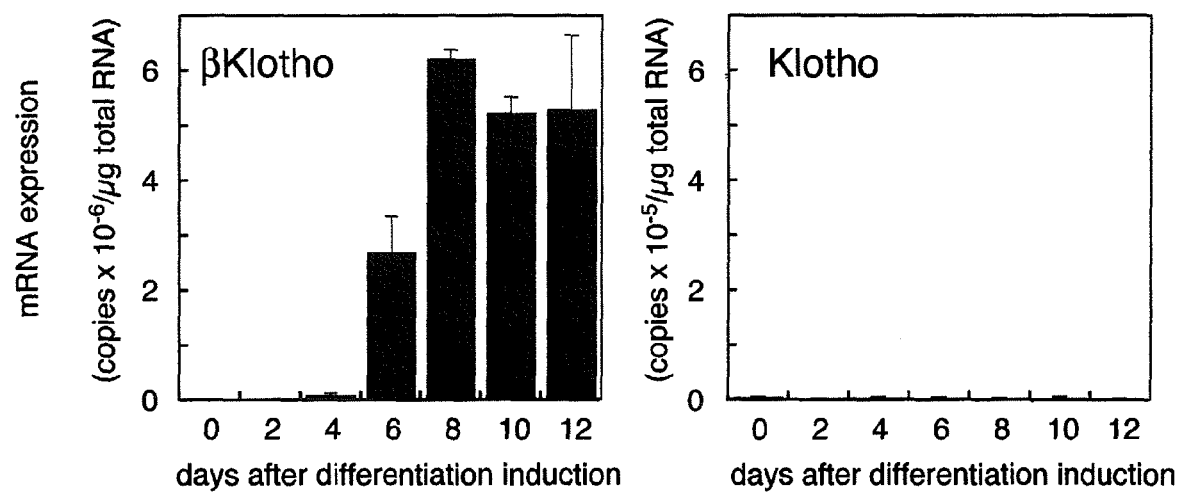
FIG. 3 is a view showing the detection results of a fluctuation in betaKlotho expression associated with differentiation into adipocytes. In the figure, the horizontal axis indicates the number of days after induction of differentiation from fibroblasts into adipocytes, and the longitudinal axis indicates the expression level of betaKlotho or Klotho mRNA. The figure suggests that betaKlotho that is expressed along with differentiation into adipocytes is closely associated with the functions of the adipocytes.

The analysis results are shown in FIG. 3. It was found that betaKlotho was expressed at a high level only in a cell differentiating into an adipocyte. In contrast, Klotho was hardly expressed both before and after differentiation. These results suggested that betaKlotho expressed associated with differentiation into adipocytes is closely related to the functions of the adipocytes. Thus, the inventors have planed to analyze the possibility that betaKlotho would be a co-receptor for FGF21 in binding to FGF receptor.

Example 4

Analysis of Necessity of BetaKlotho for Provocation of Signal Downstream of FGF Receptor Due to FGF21

The above Examples 2 and 3 suggest that the activity of FGF21 specific to adipocytes, as shown in Example 1, is induced in the coexistence of an FGF receptor and betaKlotho. Thus, in the present example, a BaF3 cell originally having no FGF receptors, which was forced to express FGFR1c, was prepared. Thereafter, the cell was further forced to express betaKlotho, or it was not forced to express such betaKloto. Subsequently, a change in the reactivity with FGF21 was analyzed.

FGFR1c-expressing BaF3 cells and FGFR1c- and betaKlotho-expressing BaF3 cells were prepared as follows. In the case of FGFR1c-expressing BaF3 cells, an animal cell expression vector into which the entire-length cDNA of mouse FGFR1c had been cloned (described in Ornitz, D. M., Xu, J., Colvin, J. S., McEwen, D. G., MacArthur, C. A., Coulier, F., Gao, G. and Goldfarb, M. (1996) Receptor specificity of the fibroblast growth factor family. J Biol Chem, 271, 15292-15297.) was introduced into BaF3 cells by an electroporation method. The cells were then cultured in the presence of G418 for approximately 2 weeks, so as to obtain drug-resistant clones. Thereafter, such clones were obtained as those capable of growing as a result of FGF1 stimulation. In the case of both FGFR1c- and betaKlotho-expressing BaF3 cells, the entire-length cDNA of mouse betaKlotho was cloned into an animal cell expression vector, and it was then introduced into the FGFR1c-expressing BaF3 cells. The cells were then cultured in the presence of Puromycin and G418 for approximately 2 weeks, so as to obtain drug-resistant clones. In the case of only betaKlotho-expressing BaF3 cells, a betaKlotho-expressing vector was introduced into BaF3 cells, and Puromycin-resistant clones were then obtained. The BaF3 cells, into which the aforementioned genes had been each introduced, were maintained in an RPMI1640 medium containing 10% FBS and interleukin 3 (IL3, supplied by adding a 5% condition medium of WEHI-3 cells). For the growth stimulation experiment, the cells were washed with an RPMI1640 medium, and they were then suspended in an RPMI1640 medium containing 10% FBS, followed by inoculating the suspension on a culture plate. Thereafter, the resultant cells were used.

The analysis results are shown in FIG. 4.

Figure 4A:
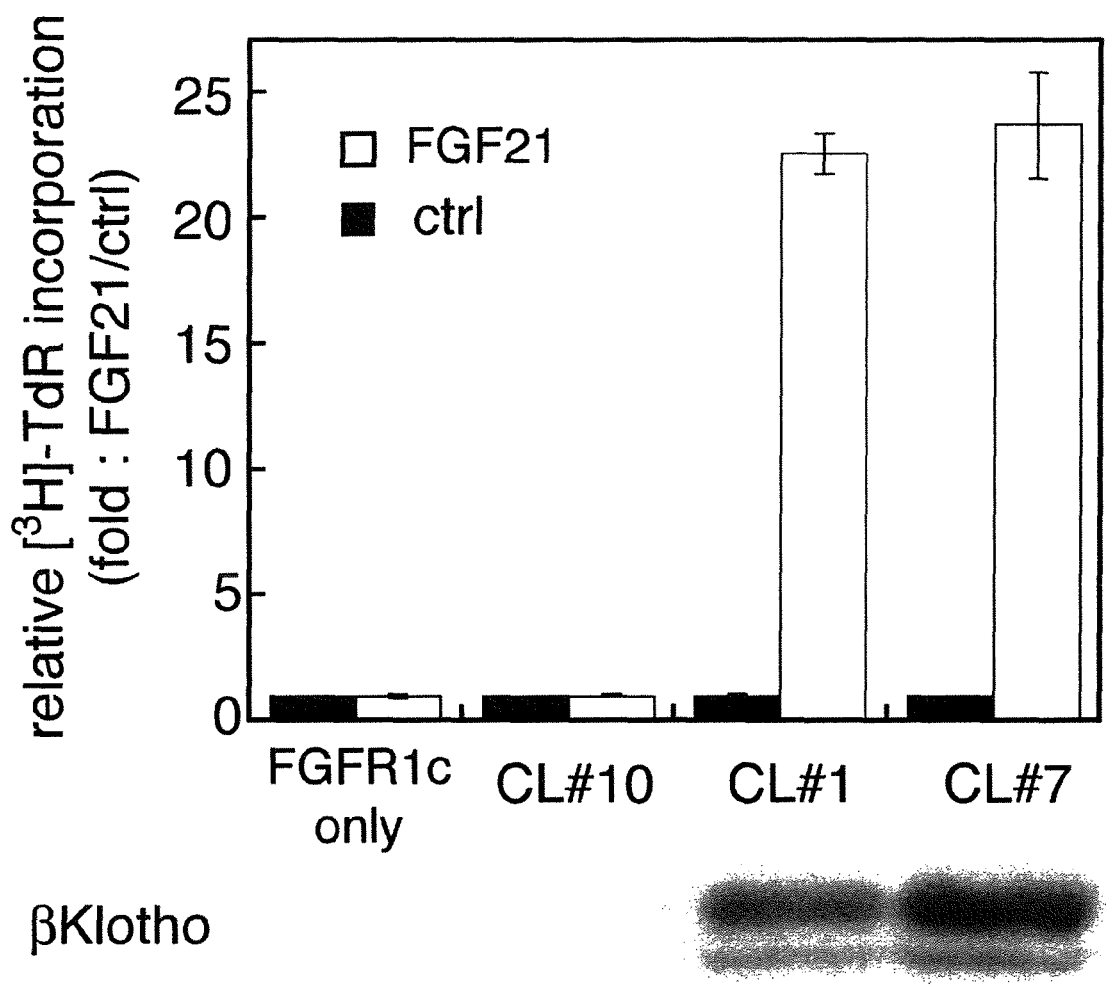
In FIG. 4A, CL#1, #7, and #10 indicate the names of BaF3 cell clones transformed by introducing both FGFR1c cDNA and betaKlotho cDNA therein. The lower case shows the results obtained by using, as materials, lysates prepared from each type of cells, and comparing the amounts of betaKlotho actually expressing as proteins by Western blot analysis with a commercially available anti-betaKlotho antibody.

In FIG. 4A, CL#1, #7, and #10 indicate the names of clones obtained by introducing both FGFR1c cDNA and betaKlotho cDNA into BaF3 cells. The lower case of FIG. 4A shows the results obtained by using, as materials, lysates prepared from each type of cells, and comparing the amounts of betaKlotho actually expressing as proteins by Western blot analysis with a commercially available anti-betaKlotho antibody. In the case of CL#10, the expression level of betaKlotho was lower than the detectable level. In the case of CL#1 and CL#7, the same level of betaKlotho expression was observed. Such betaKlotho was observed mainly as two broad bands, and the modification of N-type sugar chain was likely to take place.

Immediately after inoculation, BaF3 cells that had expressed each clone and only FGFR1c were stimulated by addition of FGF21 (open bar) or PBS (filled bar) used as a control in the presence of heparin, and they were then cultured for 42 hours. Thereafter, tritium-labeled thymidine was added to the culture solution, and the culture was further continued for 6 hours. Thereafter, the amount of thymidine incorporated into the cells was measured, so as to evaluate DNA synthesis. A DNA synthesis value obtained when the cells were not stimulated with FGF21 was defined as 1, and the ratio of a DNA synthesis value obtained by stimulating with FGF21 to the aforementioned DNA synthesis value was expressed using magnification. As a result, it was found that the cells that had expressed FGFR1c but had not expressed betaKlotho did not react with FGF21, and that only the cells that had expressed both FGFR1c and betaKlotho reacted with FGF21.

It is to be noted that the BaF3 cells that had expressed only FGFR1c did not react with FGF21 even under conditions in which heparin was present, although it was not shown in the figure.

Figure 4B:
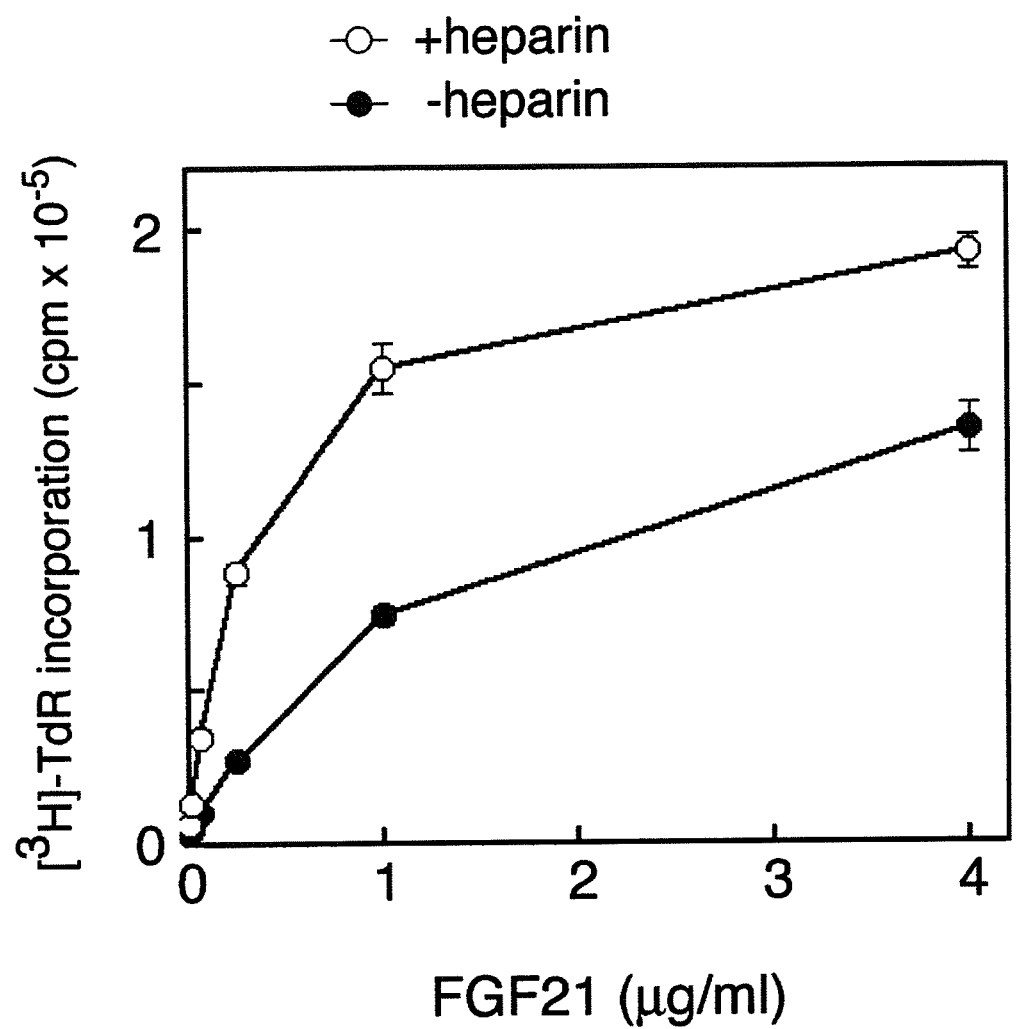
FIG. 4B shows the results obtained by measuring the amount of DNA synthesized by stimulating CL#1 cells with FGF21 while changing the amount of the FGF21. The symbol ○ indicates the presence of heparin, and the symbol ● indicates the absence of heparin.
Figure 4C:
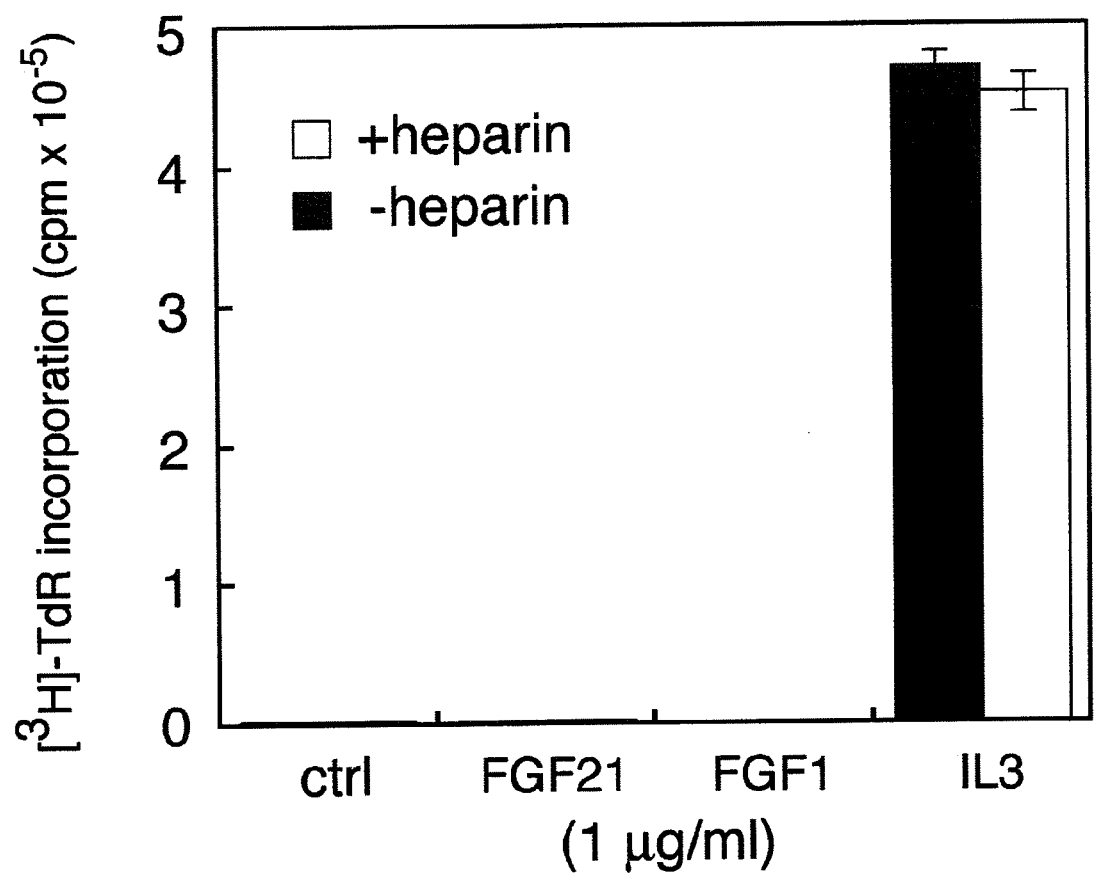
In FIG. 4C, using BaF3 cells that have not expressed FGFR1c but have expressed only betaKlotho, the ability of the cells to incorporate thymidine therein was measured. The symbol □ indicates the presence of heparin, and the symbol ■ indicates the absence of heparin. These results demonstrated that cells that have expressed FGFR1c and have not expressed betaKlotho do not react with FGF21, and that only cells that have expressed both FGFR1c and Klotho react with FGF21. The results also demonstrated that the BaF3 cells that have not expressed FGFR1c but have expressed only betaKlotho do not react with FGF21, and thus that both betaKlotho and FGFR1c are necessary for cells to react with FGF21.

FIG. 4B shows the results obtained by measuring the amount of DNA synthesized by stimulating CL#1 cells with FGF21 while changing the amount of the FGF21. Both in the presence of heparin (○) and in the absence of heparin (●), the activity of FGF21 to dose-dependently stimulate DNA synthesis was observed. In addition, it was found that heparin increases the action of FGF21. FIG. 4C shows the results obtained by examining the reactivity to FGF21 of BaF3 cells that had not expressed FGFR1c and had expressed only betaKlotho. Both in the presence of heparin (open bar) and in the absence of heparin (filled bar), the BaF3 cells did not react with FGF21. When the cells were stimulated with interleukin 3 (IL3), which was used in the maintenance of BaF3, they significantly grew.

These results demonstrated that both an FGF receptor and betaKlotho are necessary for the cells to react with FGF21.

Example 5

Figure 5:
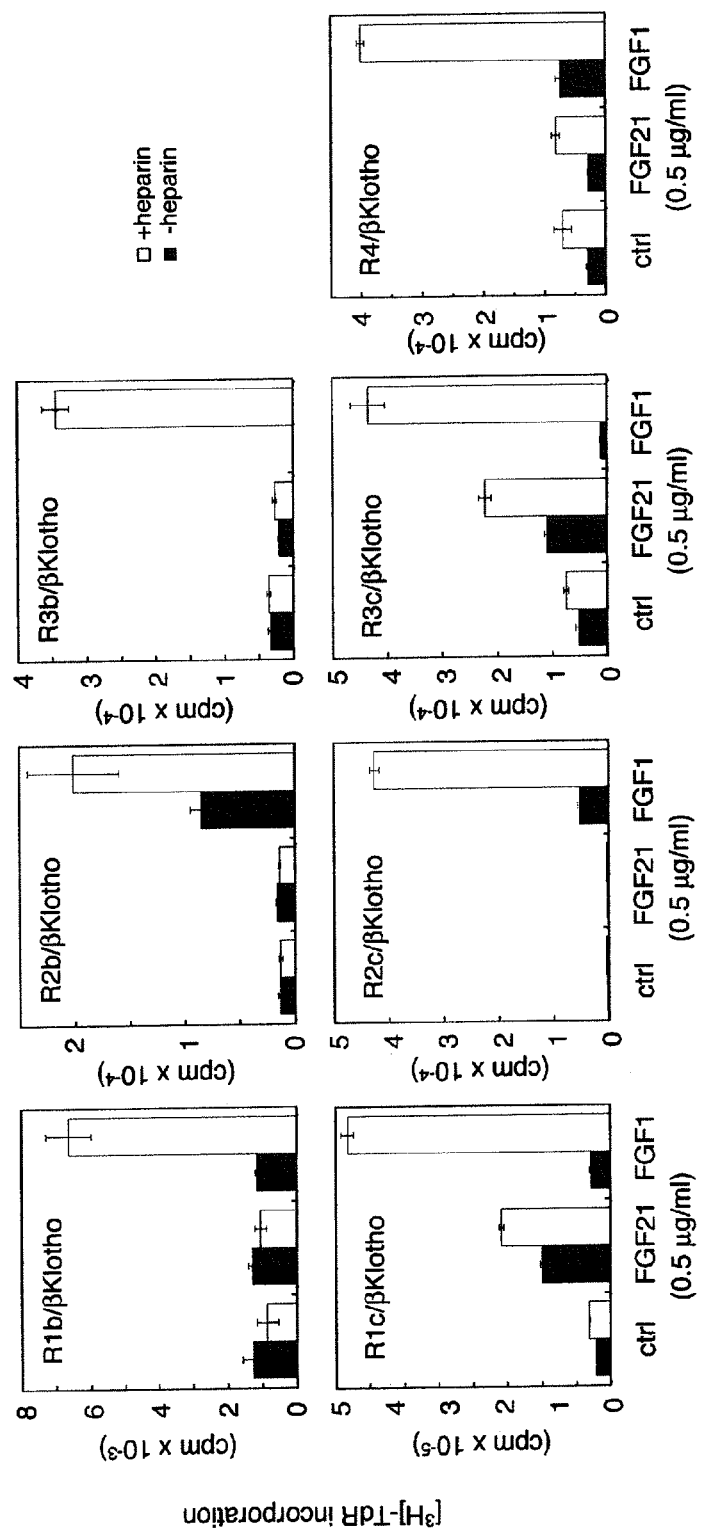
FIG. 5 is a view showing the results obtained by analyzing the specificity of an FGF receptor existing with betaKlotho when FGF21 exhibits its activity. An expression vector of such FGF receptor (FGFR1b, R1c, R2b, F2c, R3b, R3c, and R4) was introduced into BaF3 cells expressing betaKlotho, and each type of betaKlotho/FGFR-expressing cells were stimulated with FGF21 and FGF1 in the presence or absence of heparin, so that the ability of the cells to incorporate thymidine therein was measured. As a result, it was shown that both FGFR1c- and FGFR3c-expressing cells react with FGF21. In addition, in the case of the conventional FGF (typically, FGF1), its stimulus transmission activity is sharply increased in the presence of heparin. In contrast, in the case of FGF21, the presence or absence of heparin does not significantly influence on such activity.

Analysis (1) of Specificity of FGF Receptor Existing with BetaKlotho in Realization of FGF21 Activity It was demonstrated in Example 4 above that both FGFR1c as an FGF receptor and betaKlotho are necessary for reactivity to FGF21. Whether other receptor molecules can also act as such FGF receptors was examined. An expression vector containing each FGFR (FGFR1b, R1c, R2b, R2c, R3b, R3c, and R4) (described in Ornitz, D. M., Xu, J., Colvin, J. S., McEwen, D. G., MacArthur, C. A., Coulier, F., Gao, G. and Goldfarb, M. (1996) Receptor specificity of the fibroblast growth factor family. J Biol Chem, 271, 15292-15297.) was introduced into betaKlotho-expressing BaF3 cells, so as to obtain clones that were resistant to Puromycin and G418, thereby obtaining FGFR/betaKlotho-expressing cells. Such cells were stimulated with FGF21, and the amount of DNA synthesized was measured. As a result, as shown in FIG. 5, it became clear that not only FGFR1c/betaKlotho-expressing cells, but also FGFR3c/betaKlotho-expressing cells reacted with FGF21. It was also demonstrated that such reactivity was increased by the presence of heparin.

Example 6

Figure 6:
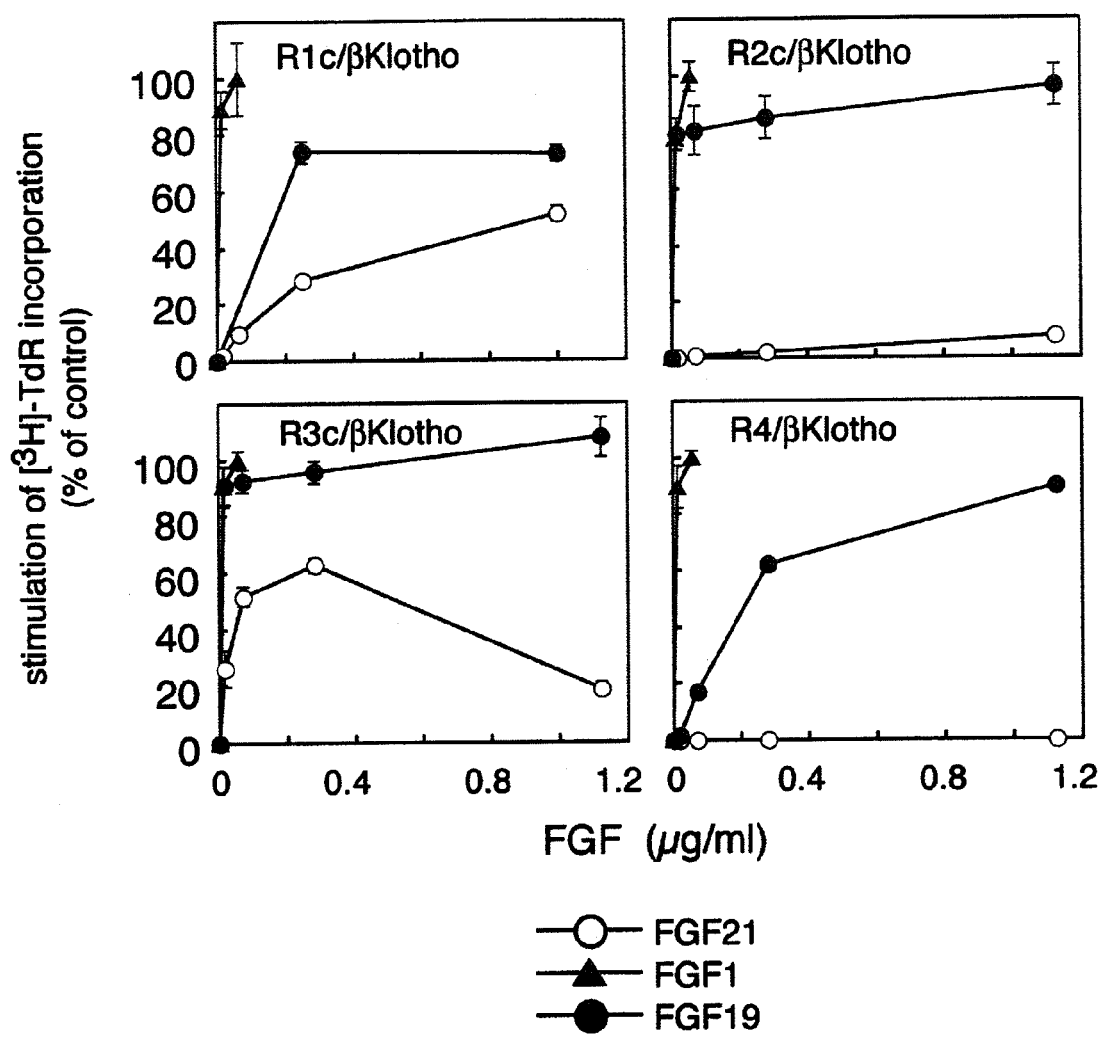
FIG. 6 is a view showing the analysis results obtained by comparing FGF19 with FGF1 in terms of the specificity of an FGF receptor existing with betaKlotho when FGF21 exhibits its activity. An expression vector of betaKlotho was introduced into BaF3 cells expressing FGFR (FGFR1c, R2c, R3c, and R4), and each type of FGFR/betaKlotho-expressing cells were stimulated with FGF21, FGF1, and FGF19 in the presence of heparin, so that the ability of the cells to incorporate thymidine therein was measured. In the figure, the symbol ○ indicates stimulation with FGF21, the symbol ● indicates stimulation with FGF19, and the symbol ▲ indicates stimulation with FGF1. As with FGF1, FGF19 reacts with all of the receptors FGFR1c, FGFR2c, FGFR3c, and FGFR4. In contrast, FGF21 reacts only with FGFR1c and FGFR3c. When the cells are stimulated with a high concentration of FGF21, they slightly react with FGFR2c.

Analysis (2) of Specificity of FGF Receptor Existing with BetaKlotho in Realization of FGF21 Activity The activity of FGF21 to stimulate the DNA synthesis of BaF3 cells that had expressed each FGFR (FGFR1c, R2c, F3c, and R4) as well as betaKlotho was compared with the activity of FGF19, which was evolutionally relative to FGF21. By procedures opposite to those of Example 5, namely, an expression vector containing betaKlotho was introduced into BaF3 cells that had expressed each type of FGFR, so as to obtain Puromycin- and G418-resistant clones, thereby obtaining FGFR/betaKlotho-expressing cells. The cells were stimulated with FGF21, FGF19, and FGF1 in the presence of heparin, while changing the amounts of FGF21, FGF19, and FGF1, as shown in the figure, and the amount of DNA synthesized was then measured. As shown in the figure, it became clear that FGF19 exhibits strong activity on all types of cells, and that, in contrast, FGF21 activates only R1c/betaKlotho-expressing cells and R3c/betaKlotho-expressing cells (FIG. 6).

Example 7

Analysis of Activation of Intracellular Signaling Molecule Associated with Stimulation with FGF21

Each FGFR/betaKlotho-expressing cells obtained in Example 6 were stimulated with FGF, and the activated state (phosphorylated state) of a signaling molecule FRS2 (fibroblast growth factor receptor substrate 2) located downstream of FGFR, and that of MAPK (mitogen activated protein kinase; alias: ERK (extracellular signal-regulated kinase; in general, there are two types of ERKs, namely, ERK1 with a molecular weight of 44 kDa and ERK2 with a molecular weight of 42 kDa)), were analyzed. Different types of cells were stimulated with each FGF in the presence of heparin for 10 minutes, and a cell lysate was then prepared. Thereafter, the phosphorylated degree was evaluated by measuring it by a Western blotting method using a commercially available anti-phosphorylation FRS2 antibody or an anti-phosphorylation MAPK antibody.

Figure 7:
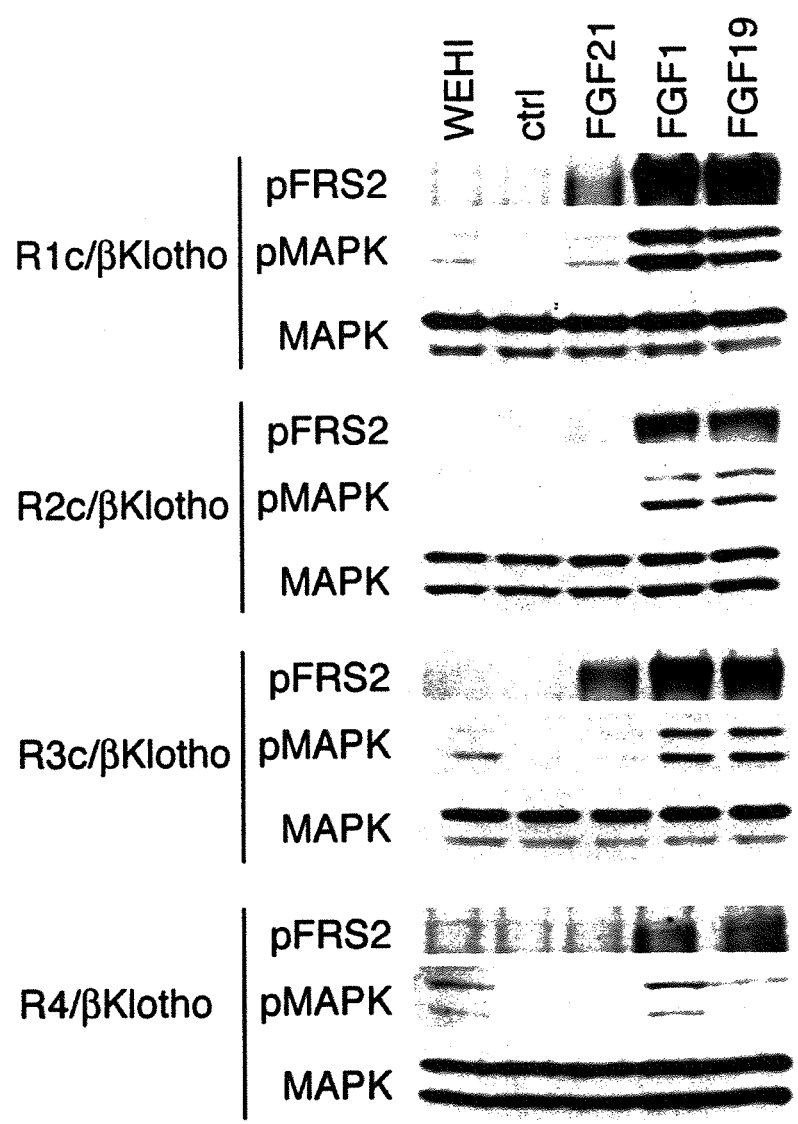
FIG. 7 is a view showing the analysis results of the activation of intracellular signal transmission molecules associated with stimulation with FGF21. Different types of FGFR/betaKlotho-expressing cells were each stimulated with FGF21, FGF1, and FGF19. Thereafter, the phosphorylation of FGFR downstream signal transmission substances, FRS2 and MAPK, was measured using an anti-phosphorylated FRS2 antibody (the former case) or using an anti-phosphorylated ERK1/2 antibody (the latter case). In the figure, the term "WEHI" means that a culture supernatant of WEHI as an IL-3-secreting cell was added. FGF19 and FGF1 increase the phosphorylation of FRS2 and that of MAPK in cells expressing all of the receptors FGFR1c, FGFR2c, FGFR3c, and FGFR4, as well as betaKlotho. In contrast, FGF21 increases the phosphorylation of FRS2 and that of MAPK only in FGFR1c/betaKlotho-expressing cells and FGFR3c/betaKlotho-expressing cells.

The results are shown in FIG. 7. In the figure, each MAPK column indicates the amount of total MAPK in the cell lysate measured by a Western blotting using an anti-ERK1/2 antibody. The total amount of MAPK (ERK1/2) in stimulated cells or in unstimulated control cells was not changed. It was demonstrated that FGF1 and FGF19 significantly increase the phosphorylation of FRS2 and MAPK in all types of cells, and that, in contrast, FGF21 increases the phosphorylation of FRS2 and MAPK in R1c/betaKlotho-expressing cells and in R3c/betaKlotho-expressing cells. These results well reflect the results of Example 6.

Example 8

Figure 8:
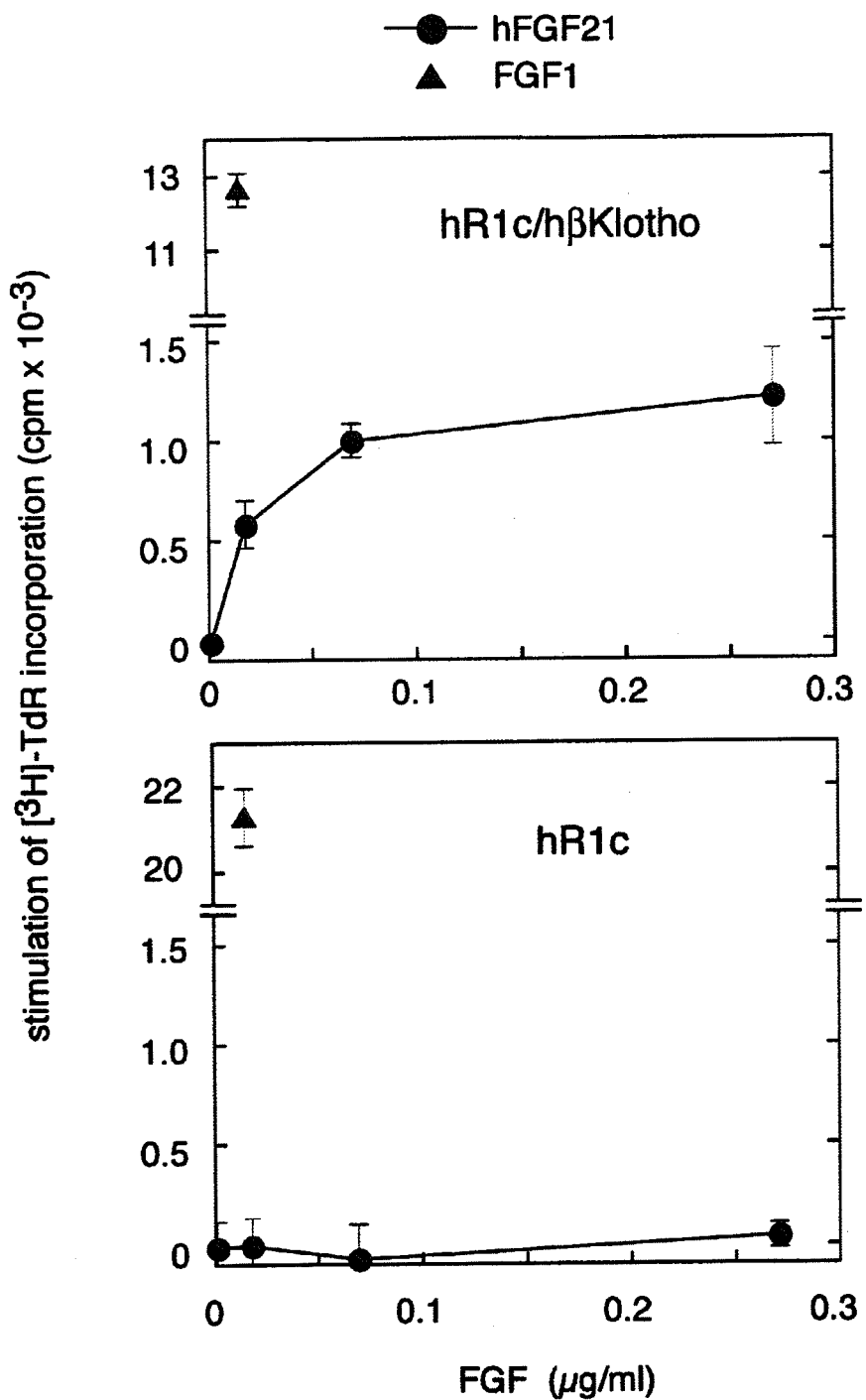
FIG. 8 is a view showing the analysis results of the activity of humanized FGF21 on cells that have co-expressed humanized FGFR1c and humanized betaKlotho each having a human amino acid sequence. Humanized FGFR1c (hR1c)-expressing BaF3 cells or humanized FGFR1c/humanized betaKlotho (hβKlotho)-expressing cells were stimulated with humanized FGF21 (hFGF21) or FGF1 in the presence of 10 μg/ml heparin, so that the ability of the cells to incorporate thymidine therein was measured. In the figure, the symbol ● indicates stimulation with hFGF21, and the symbol ▲ indicates stimulation with FGF1. FGF1 acted on both types of cells. However, humanized FGF21 only acted on the humanized FGFR1c/humanized betaKlotho-expressing cells, and it increased the amount of thymidine incorporated into the cells in a dose-dependent manner.

Analysis of Activity of Humanized FGF21 on Cells that have Co-Expressed Humanized FGFR1c and Humanized BetaKlotho Each Having Human Amino Acid Sequence In Examples 4, 5, 6, and 7, it was shown that FGF21 reacts with FGFR1c in the presence of betaKlotho. FGFR1c, betaKlotho, FGF21, and the like, which were used in an actual experimental system, were all derived from mice used as typical mammalian models. With regard to these molecules, the homology between a human and a mouse at the amino acid sequence level is extremely high (80% in FGF21, 78% in betaKlotho, and 98% in FGFR1). As a result, naturally, there are no problems regarding the compatibility of the human with the mouse, and thus it is clear that the same results as those from a murine molecule will be obtained even using a humanized molecule. In the present example, as a precautionary measure, an experimental system using a humanized molecule was constructed to confirm such respect, and an experiment was carried out. Specifically, the humanized cDNA of FGFR1c and that of betaKlotho were prepared from a commercially available human RNA sample (Takara Bio Inc.) by PCR. FGFR1c was introduced into an expression vector having an SRalpha promoter (pSRalpha), and betaKlotho was introduced into an expression vector having a CMV promoter (pcDNA3.1; Invitrogen). As with Example 4, an FGFR1c expression vector was introduced into BaF3 cells by an electroporation method, and FGFR1c-expressing BaF3 cells were obtained as G418-resistant clones. FGFR1c/betaKlotho-co-expressing cells were obtained as Puromycin-resistant clones by introducing a betaKlotho expression vector into FGFR1c-expressing BaF3 cells. A humanized FGF21 protein was prepared as follows. The cDNA of humanized FGF21 was prepared from a commercially available human RNA sample (Takara Bio Inc.) by PCR, and it was then introduced into an expression vector used for *Escherichia coli*. Using this vector, a protein was prepared in accordance with the method described in Non-Patent Document 1. In the presence of heparin, humanized FGF21 was added in various types of concentrations to FGFR1c-expressing cells or FGFR1c/betaKlotho-co-expressing cells, and the amount of DNA synthesized was then measured. The results are shown in FIG. 8. Regardless of the presence or absence of the expression of betaKlotho, FGF1 used as a control promoted the DNA synthesis in the cells. In contrast, FGF21 activated only the FGFR1c/betaKlotho-co-expressing cells.

These results attested that the initial assumption to the effect that the same results as the experimental results of each example using mouse-derived molecules could be obtained was correct.

Example 9

Figure 9:
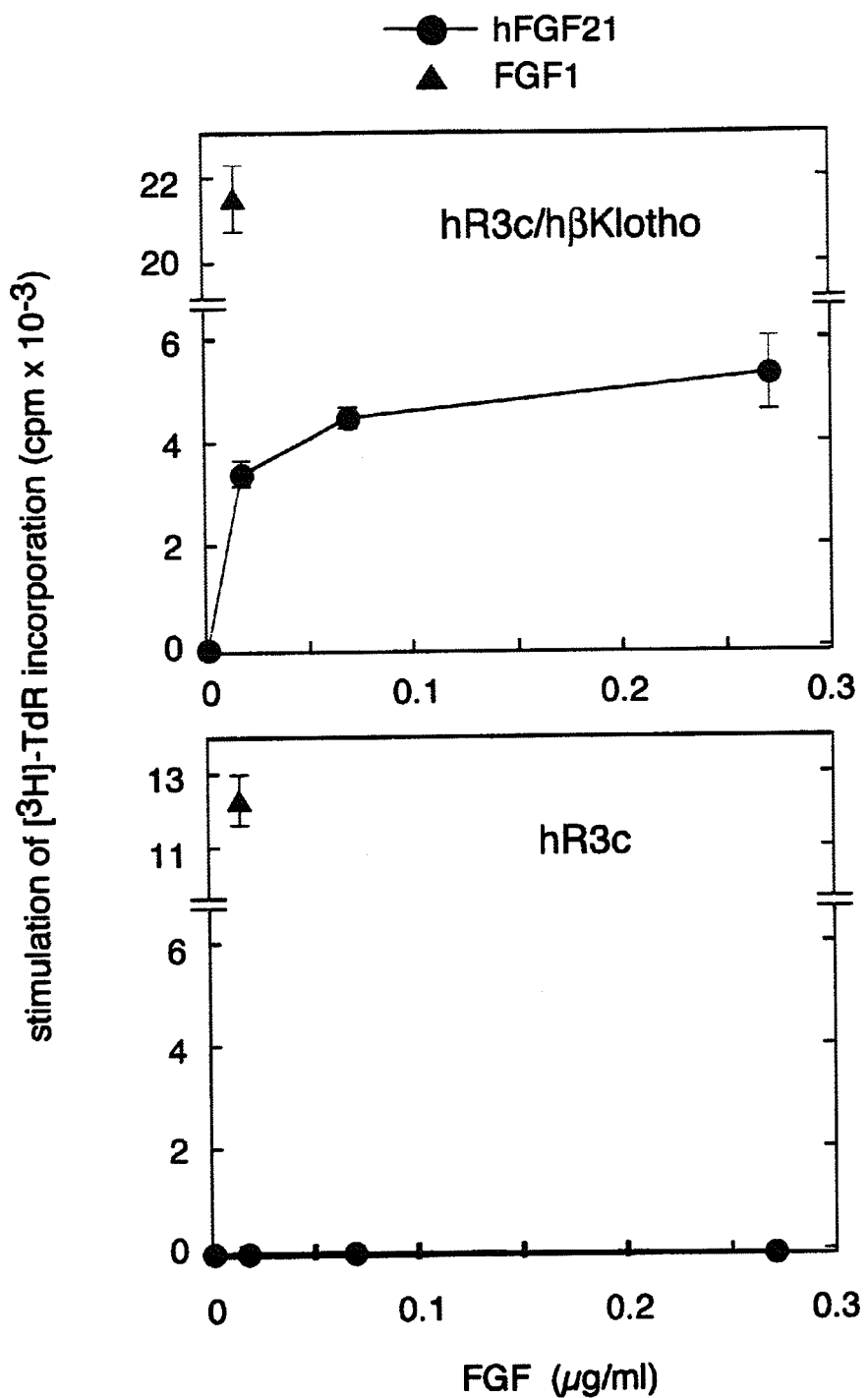
FIG. 9 is a view showing the analysis results of the activity of humanized FGF21 on cells that have co-expressed humanized FGFR3c and humanized betaKlotho each having a human amino acid sequence. Humanized FGFR3c (hR3c)-expressing BaF3 cells or humanized FGFR3c/humanized betaKlotho (hβKlotho)-expressing cells were stimulated with humanized FGF21 (hFGF21) or FGF1 in the presence of 10 μg/ml heparin, so that the ability of the cells to incorporate thymidine therein was measured. In the figure, the symbol ● indicates stimulation with hFGF21, and the symbol ▲ indicates stimulation with FGF1. FGF1 acted on both types of cells. However, humanized FGF21 only acted on the humanized FGFR3c/humanized betaKlotho-expressing cells, and it increased the amount of thymidine incorporated into the cells in a dose-dependent manner.

Analysis of Activity of Humanized FGF21 on Cells that have Co-Expressed Humanized FGFR3c and Humanized BetaKlotho Each Having Human Amino Acid Sequence The homology between human FGFR3 and mouse FGFR3 at the amino acid sequence level is 93%. An experiment was carried out to demonstrate that, even in the case of humanized FGFR3c, the same results as those of murine FGFR3c would be obtained. The cDNA of humanized FGFR3c was prepared from a commercially available human RNA sample (Takara Bio Inc.) by PCR. The sequence of its intracellular portion was substituted with the sequence of humanized FGFR1, and it was then introduced into an expression vector having an SRalpha promoter (pSRalpha). The FGFR3c expression vector was introduced into BaF3 cells by an electroporation method, so as to obtain FGFR3c-expressing BaF3 cells as G418-resistant clones. In the case of FGFR3c/betaKlotho-co-expressing cells, a betaKlotho expression vector was introduced into the FGFR3c-expressing BaF3 cells, so as to obtain the aforementioned cells as Puromycin-resistant clones. In the presence of heparin, humanized FGF21 was added in various types of concentrations to FGFR3c-expressing cells or FGFR3c/betaKlotho-co-expressing cells, and the amount of DNA synthesized was then measured. The results are shown in FIG. 9. Regardless of the presence or absence of the expression of betaKlotho, FGF1 used as a control promoted the DNA synthesis in the cells. In contrast, FGF21 activated only the FGFR3c/betaKlotho-co-expressing cells. These experimental results also demonstrated that the same results as those of a murine molecule can be obtained from a humanized molecule.

Example 10

Analysis of Specificity of BetaKlotho Existing with FGF Receptor in Realization of FGF21 Activity In order to confirm that betaKlotho is a co-receptor specific to FGF21 in binding to an FGF receptor, betaKlotho was allowed to act on FGF23 having high structural similarity to FGF21, and Klotho having high structural similarity to betaKlotho was allowed to act on FGF21. Thereafter, the level of compatibility was examined in each case.

Specifically, BaF3 cell that had co-expressed FGFR1c and betaKlotho and BaF3 cells that had co-expressed FGFR1c and Klotho were prepared by the same transformation method and under the same culture conditions as those applied in Example 4. Thereafter, FGF21 and FGF23 were added to both types of transformed cells in the presence or absence of heparin, and the amount of DNA synthesized was then measured.

Figure 10:
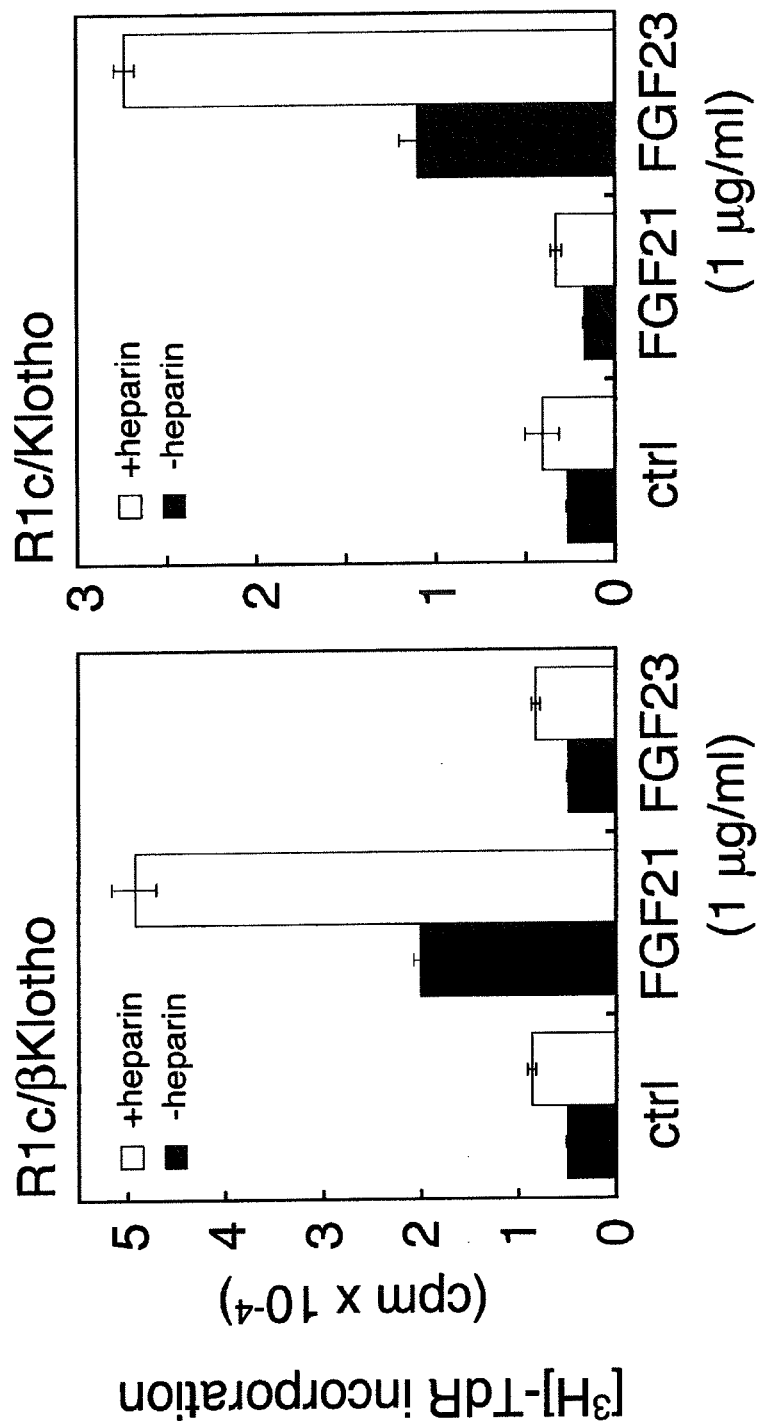
FIG. 10 is a characteristic view showing the analysis results of the specificity of Klotho existing with an FGF receptor when FGF21 exhibits its activity. FGF21 and FGF23 were added to BaF3 cells expressing betaKlotho as well as FGFR1c, and to BaF3 cells expressing Klotho as well as FGR1c, in the presence or absence of heparin. Thereafter, the ability of the cells to incorporate thymidine therein was measured. In the case of Klotho, the cells did not react with FGF21. In addition, FGF23 reacting with the cells in the presence of FGFR1c and Klotho was examined. As a result, even if the cells had expressed both FGFR1c and betaKlotho, they did not react with FGF23.

The results are shown in FIG. 10. Regardless of the presence or absence of heparin, FGF21 did not react with FGFR1c even in the presence of Klotho. On the contrary, in the case of FGF23, regardless of the presence or absence of heparin, FGF23 did not react with FGFR1c even in the presence of betaKlotho.

Thus, it was shown that only the combination of FGF21 with betaKlotho and the combination of FGF23 with Klotho are able to act on FGFR1c-expressing cells. Accordingly, it was demonstrated that betaKlotho is a co-receptor specific to FGF21 in binding to FGF receptor.

Example 11

Detection of Formation of Complex of BetaKlotho with FGF21 or FGF Receptor

In Examples 4 to 10, it was demonstrated in a cell biological manner that betaKlotho is necessary for the expression of the action of FGF21 mediated by an FGF receptor.

In the present example, the formation of a complex between betaKlotho and an FGF receptor or FGF21 was examined in a biochemical manner. Specifically, a V5 tag and a His tag were added to the C-terminus of the extracellular domain of betaKlotho in a tandem manner to prepare a soluble protein. Thereafter, the soluble betaKlotho protein was incubated with FGF21 in a test tube in the presence or absence of heparin, and betaKlotho was then precipitated using anti-V5 tag antibody-immobilized beads. Whether or not FGF21 bound to betaKlotho and was co-precipitated therewith was analyzed by an immunoblotting method.

Figure 11:
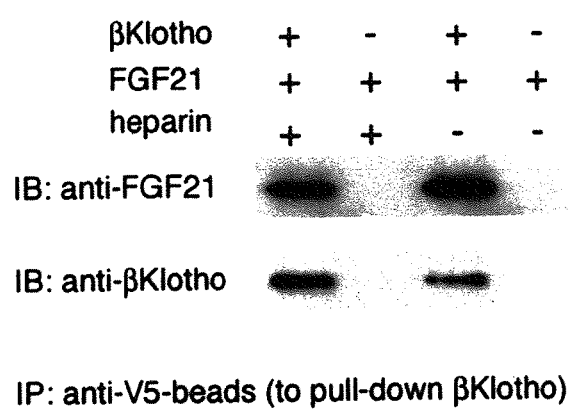
FIG. 11 is a view showing the detection results of a complex formed between betaKlotho and FGF21 or an FGF receptor. A soluble betaKlotho protein and FGF21 were incubated in the presence or absence of heparin, and betaKlotho was then precipitated using anti-V5 tag antibody-immobilized beads. Thereafter, whether or not FGF21 bound to betaKlotho and was also precipitated with the betaKlotho was analyzed by an immunoblotting method. Such betaKlotho and FGF21 physically form a complex, regardless of the presence or absence of heparin. Moreover, betaKlotho physically forms a complex also with all of the receptors FGFR1c, FGFR2c, FGFR3c, and FGFR4.
Figure 11:
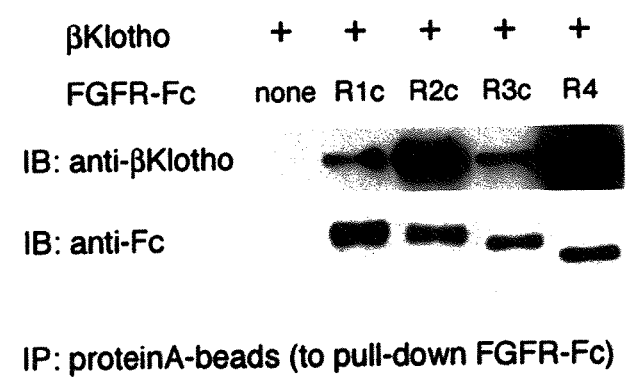

The results are shown in FIG. 11A). Regardless of the presence or absence of heparin, FGF21 was precipitated in the presence of betaKlotho. From these results, it was confirmed that the binding of betaKlotho to FGF21 is formed regardless of the presence or absence of heparin.

Moreover, the soluble betaKlotho protein and a fusion protein obtained by adding an immunoglobulin Fc domain to the extracellular domain of an FGF receptor (FGFR-Fc; manufactured by R&D Systems) were incubated, and FGFR-Fc was then precipitated using protein A beads. Whether or not betaKlotho bound to FGFR-Fc and was co-precipitated therewith was analyzed.

The results are shown in FIG. 11B). The results demonstrated that betaKlotho was precipitated depending on the presence of FGFR-Fc. It became clear that betaKlotho binds to all of FGF receptor subtypes R1c, R2c, R3c, and R4.

Example 12

Analysis Occurring by FGF21 Stimulation of Undifferentiated 3T3-L1 Cells Forced to Express BetaKlotho It was demonstrated in Example 1 that FGF21 acts on adipocytes to increase the mRNA level of GLUT1, but that FGF21 does not exhibit such activity on cells before differentiation. Moreover, it was demonstrated in Example 2 that the expression level of betaKlotho increases associated with the differentiation of adipocytes. Furthermore, in Examples 3 to 10, it was demonstrated using BaF3 cells that betaKlotho is a co-receptor for FGF21 in binding to FGF receptor.

Hence, in the present example, whether or not betaKlotho functions as a co-receptor for FGF21 in binding to FGF receptor even in 3T3-L1 cells that has not yet differentiated into adipocytes was analyzed. A betaKlotho expression vector produced by the method described in Example 4 and an empty vector used as a control, into which betaKlotho cDNA had not been inserted, were introduced into 3T3-L1 fibroblasts cultured as described in Example 1 by a lipofection method, thereby obtaining Puromycin-resistant clones. These different types of cells were stimulated with FGF21, and 10 minutes after the stimulation, a cell lysate was prepared. The activation of FRS2 and MAPK that were signaling molecules located downstream of FGFR was examined by a Western blotting method.

Figure 12:
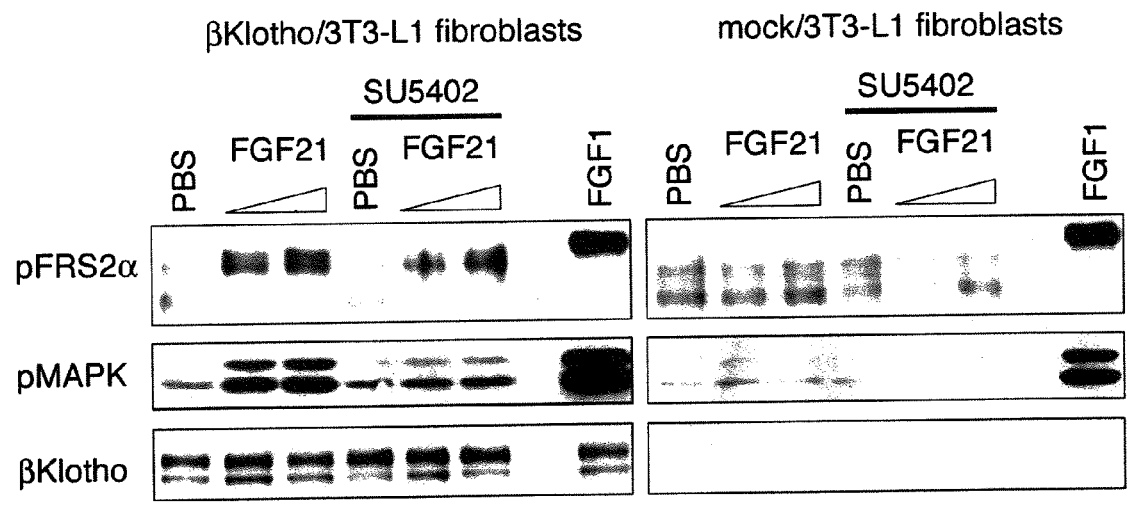
FIG. 12 is a view showing the analysis results of signaling occurring when undifferentiated 3T3-L1 cells which had been forced to express betaKlotho was stimulated with FGF21. 3T3-L1 fibroblasts which had been allowed to express betaKlotho were stimulated with FGF21, and the activation (phosphorylation) of signal transmission molecules FRS2 and MAPK located downstream of FGFR was examined by a Western blotting method. In the figure, the term "PBS" indicates 10 µl of a Dulbecco's modified phosphate buffered saline added to a system, and the term "SU5402" indicates a 10 µM FGF receptor tyrosine kinase inhibitor added to a system. Two types of concentrations of FGF21 added were applied (1.1 µg/ml and 4.5 µg/ml). Even if undifferentiated 3T3-L1 cells that had not expressed betaKlotho were stimulated with FGF21, the phosphorylated state of FRS2 and that of MAPK do not change. In the case of the undifferentiated 3T3-L1 cells which had been forced to express betaKlotho, the amount of FRS2 phosphorylated and that of MAPK phosphorylated increase depending on stimulation with FGF21. The phosphorylated level of FRS2 and that of MAPK associated with FGF21 stimulation decrease as a result of treatment with the FGF receptor tyrosine kinase inhibitor SU5402.

The results are shown in FIG. 12. As shown in the figure, it was demonstrated that only the cells into which the betaKlotho expression vector had been introduced reacted with stimulation with FGF21, and as a result, the phosphorylation levels of FRS2 and MAPK were increased. In addition, when the cells pre-treated with a tyrosine kinase inhibitor of FGFR, SU5402 (manufactured by Merck), for 3 hours, were stimulated with FGF21, the degree of phosphorylation decreased. These results demonstrated that the activity of FGF21 is transmitted via FGFR.

Example 13

Analysis of Expression of GLUT1 mRNA by FGF21 Stimulation of Undifferentiated 3T3-L1 Cells Forced to Express BetaKlotho Using the 3T3-L1 fibroblasts forced to express betaKlotho, produced in Example 12, a change in the mRNA level of GLUT1 (glucose transporter 1) depending on the amount of stimulating FGF21 was examined.

A betaKlotho expression vector or an empty vector used as a control, into which betaKlotho cDNA had not been inserted, were introduced into 3T3-L1 fibroblasts, and FGF21 was then added in various types of concentrations to a culture solution of the 3T3-L1 fibroblasts. The obtained mixture was cultured for 6 hours. Thereafter, RNA was extracted, and the mRNA level of GLUT1 was then measured.

Figure 13:
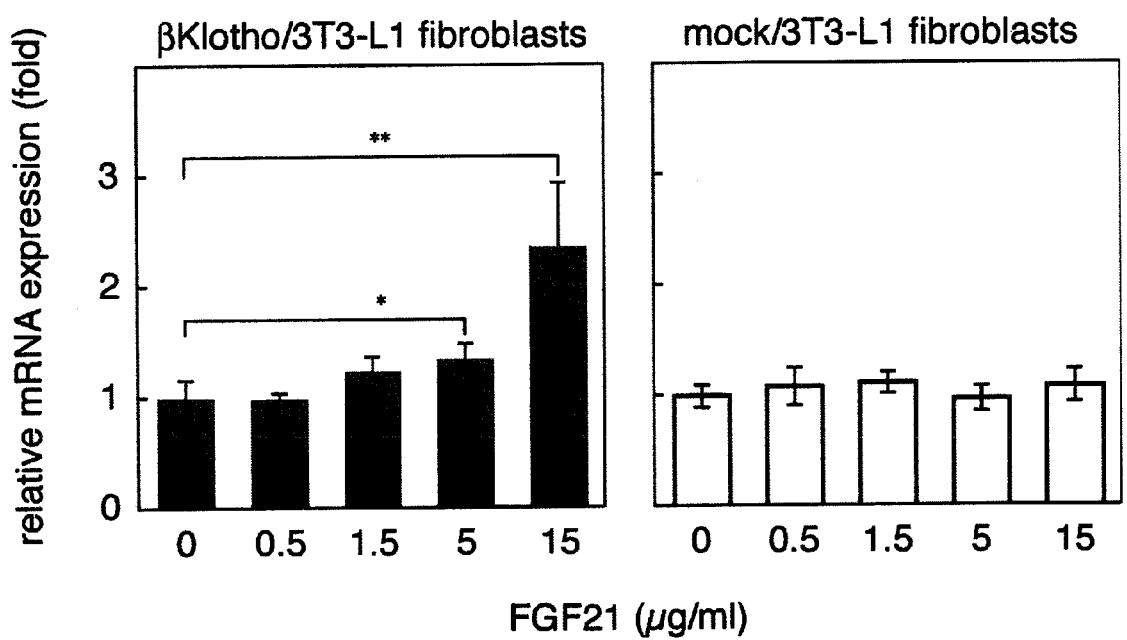
FIG. 13 is a view showing the analysis results of the expression of GLUT1 mRNA, when the undifferentiated 3T3-L1 cells which had been forced to express betaKlotho was stimulated with FGF21. 3T3-L1 fibroblasts which had been allowed to express betaKlotho were stimulated with FGF21, and a change in the level of GLUT1 mRNA was examined. As a control, there were used 3T3-L1 fibroblasts into which an empty vector containing no betaKlotho cDNA had been introduced. Even if undifferentiated 3T3-L1 fibroblasts that had not expressed betaKlotho were stimulated with FGF21, the expression level of GLUT1 mRNA does not change. In the case of the undifferentiated 3T3-L1 cells which had been forced to express betaKlotho, the expression level of GLUT1 mRNA increases depending on the concentration of stimulating FGF21.

As shown in FIG. 13, it was clearly found that the mRNA level of GLUT1 increased depending on the amount of FGF21 added to the culture solution of the 3T3-L1 fibroblasts forced to express betaKlotho (in the figure, the symbol * indicates that there is a significant difference at a risk percentage of less than 5% in a Student's t test, and the symbol ** indicates that there is a significant different at a risk percentage of less than 1% in such Student's t-test). On the other hand, a change in the mRNA level of GLUT1 was not observed in the control 3T3-L1 fibroblasts by the addition of FGF21. From these results, it became clear that even if the cells are 3T3-L1 cells before differentiation into adipocytes, if the cells are forced to express betaKlotho, the cells receive FGF21 stimulation and increase the expression level of GLUT1.

The invention claimed is:

1. A method for screening a test substance for activation of a receptor associated with FGF21 activity which comprises:
    (a) introducing FGFR1c and FGFR3c genes and a betaKlotho gene into a cell that has endogenously expressed neither an FGF receptor nor betaKlotho, then allowing said test substance to act on a transformed cell expressing the FGFR1c or FGFR3c and the betaKlotho on the surface thereof and determining whether said test substance induced increased growth of said transformed cell or increased signalling activity in said transformed cell when compared with a transformed cell on which no test substance had acted;
    (b) introducing an FGFR4 gene and a betaKlotho gene into a cell that has endogenously expressed neither an FGF receptor nor betaKlotho, then allowing said test substance to act on a transformed cell expressing the FGFR4 and the betaKlotho on the surface thereof and determining whether said test substance induced neither increased growth of said transformed cell nor increased signalling activity in said transformed cell when compared with a transformed cell on which no test substance had acted and
    (c) introducing FGFR1c, FGFR2c or FGFR3c genes into a cell that has endogenously expressed neither an FGF receptor nor a betaKlotho then allowing said test substance to act on a transformed cell expressing the FGFR1c, FGFR2c or FGFR3c on the surface thereof and determining whether said test substance induced neither increased growth of said transformed cell nor increased signaling activity in said transformed cell as is the case with a transformed cell on which no test substance had acted;
    whereby a positive showing in step (a) and a negative showing in steps (b) and (c) indicate activation of said receptor.

* * * * *

SEQUENCE LISTING

<160> NUMBER OF SEQ ID NOS: 9

<210> SEQ ID NO 1
<211> LENGTH: 3132
<212> TYPE: DNA
<213> ORGANISM: mouse

<400> SEQUENCE: 1

| | | | | | | |
|---|---|---|---|---|---|---|
| atgaagacag | gctgtgcagc | agggtctccg | gggaatgaat | ggattttctt | cagctctgat | 60 |
| gaaagaaaca | cacgctctag | gaaaacaatg | tccaacaggg | cactgcaaag | atctgccgtg | 120 |
| ctgtctgcgt | ttgttctgct | gcgagctgtt | accggcttct | ccggagacgg | gaaagcaata | 180 |
| tgggataaaa | aacagtacgt | gagtccggta | aacccaagtc | agctgttcct | ctatgacact | 240 |
| ttccctaaaa | acttttcctg | gggcgttggg | accggagcat | tcaagtggaa | agggagttgg | 300 |
| aagacagatg | gaagaggacc | ctcgatctgg | gatcggtacg | tctactcaca | cctgagaggt | 360 |
| gtcaacggca | cagacagatc | cactgacagt | tacatctttc | tggaaaaaga | cttgttggct | 420 |
| ctggattttt | taggagtttc | ttttatcag | ttctcaatct | cctggccacg | gttgtttccc | 480 |
| aatggaacag | tagcagcagt | gaatgcgcaa | ggtctccggt | actaccgtgc | acttctggac | 540 |
| tcgctggtac | ttaggaatat | cgagcccatt | gttaccttgt | accattggga | tttgcctctg | 600 |
| acgctccagg | aagaatatgg | gggctggaaa | aatgcaacta | tgatagatct | cttcaacgac | 660 |
| tatgccacat | actgcttcca | gacctttgga | gaccgtgtca | atattggat | tacaattcac | 720 |
| aaccccttacc | ttgttgcttg | gcatgggttt | ggcacaggta | tgcatgcacc | aggagagaag | 780 |
| ggaaatttaa | cagctgtcta | cactgtggga | cacaacctga | tcaaggcaca | ttcgaaagtg | 840 |
| tggcataact | acgacaaaaa | cttccgccct | catcagaagg | gttggctctc | catcaccttg | 900 |
| gggtcccatt | ggatagagcc | aaacagaaca | gacaacatgg | aggacgtgat | caactgccag | 960 |
| cactccatgt | cctctgtgct | tggatggttc | gccaacccca | tccacgggga | cggcgactac | 1020 |
| cctgagttca | tgaagacggg | cgccatgatc | cccgagttct | ctgaggcaga | aaggaggag | 1080 |
| gtgaggggca | cggctgattt | cttttgccttt | tccttcgggc | ccaacaactt | caggccctca | 1140 |
| aacaccgtgg | tgaaaatggg | acaaaatgta | tcactcaact | taaggcaggt | gctgaactgg | 1200 |
| attaaactgg | aatacgatga | ccctcaaatc | ttgatttcgg | agaacggctg | gttcacagat | 1260 |
| agctatataa | agacagagga | caccacggcc | atctacatga | tgaagaattt | cctaaaccag | 1320 |
| gttcttcaag | caataaaatt | tgatgaaatc | cgcgtgtttg | gttatacggc | ctggactctt | 1380 |
| ctggatggct | ttgagtggca | ggatgcctat | acgacccgac | gagggctgtt | ttatgtggac | 1440 |
| tttaacagtg | agcagaaaga | gaggaaaccc | aagtcctcgg | ctcattacta | caagcagatc | 1500 |
| atacaagaca | acggcttccc | tttgaaagag | tccacgccag | acatgaaggg | tcggttcccc | 1560 |
| tgtgatttct | cttggggagt | cactgagtct | gttcttaagc | ccgagtttac | ggtctcctcc | 1620 |
| ccgcagttta | ccgatcctca | cctgtatgtg | tggaatgtca | ctggcaacag | attgctctac | 1680 |
| cgagtggaag | gggtaaggct | gaaaacaaga | ccatcccagt | gcacagatta | tgtgagcatc | 1740 |
| aaaaaacgag | ttgaaatgtt | ggcaaaaatg | aaagtcaccc | actaccagtt | tgctctggac | 1800 |
| tggacctcta | tccttcccac | tggcaatctg | tccaaagtta | acagacaagt | gttaaggtac | 1860 |
| tataggtgtg | tggtgagcga | aggactgaag | ctgggcgtct | tccccatggt | gacgttgtac | 1920 |
| cacccaaccc | actcccatct | cggcctcccc | ctgccacttc | tgagcagtgg | ggggtggcta | 1980 |
| aacatgaaca | cagccaaggc | cttccaggac | tacgctgagc | tgtgcttccg | ggagttgggg | 2040 |

```
gacttggtga agctctggat caccatcaat gagcctaaca ggctgagtga catgtacaac    2100
cgcacgagta atgacaccta ccgtgcagcc cacaacctga tgatcgccca tgcccaggtc    2160
tggcacctct atgataggca gtataggccg gtccagcatg gggctgtgtc gctgtcctta    2220
cattgcgact gggcagaacc tgccaacccc tttgtggatt cacactggaa ggcagccgag    2280
cgcttcctcc agtttgagat cgcctggttt gcagatccgc tcttcaagac tggcgactat    2340
ccatcggtta tgaaggaata catcgcctcc aagaaccagc gagggctgtc tagctcagtc    2400
ctgccgcgct tcaccgcgaa ggagagcagg ctggtgaagg gtaccgtcga cttctacgca    2460
ctgaaccact tcactacgag gttcgtgata cacaagcagc tgaacaccaa ccgctcagtt    2520
gcagacaggg acgtccagtt cctgcaggac atcacccgcc taagctcgcc cagccgcctg    2580
gctgtaacac cctggggagt gcgcaagctc cttgcgtgga tccggaggaa ctacagagac    2640
agggatatct acatcacagc caatggcatc gatgacctgg ctctagagga tgatcagatc    2700
cgaaagtact acttggagaa gtatgtccag gaggctctga agcatatctc cattgacaag    2760
gtcaaaatca aaggctacta tgcattcaaa ctgactgaag agaaatctaa gcctagattt    2820
ggattttttca cctctgactt cagagctaag tcctctgtcc agttttacag caagctgatc    2880
agcagcagtg gcctccccgc tgagaacaga agtcctgcgt gtggtcagcc tgcggaagac    2940
acagactgca ccatttgctc atttctcgtg gagaagaaac cactcatctt cttcggttgc    3000
tgcttcatct ccactctggc tgtactgcta tccatcaccg ttttcatca tcaaaagaga    3060
agaaaattcc agaaagcaag gaacttacaa aatataccat tgaagaaagg ccacagcaga    3120
gttttcagct aa                                                       3132
```

<210> SEQ ID NO 2
<211> LENGTH: 1043
<212> TYPE: PRT
<213> ORGANISM: mouse

<400> SEQUENCE: 2

```
Met Lys Thr Gly Cys Ala Ala Gly Ser Pro Gly Asn Glu Trp Ile Phe
1               5                   10                  15

Phe Ser Ser Asp Glu Arg Asn Thr Ser Arg Lys Thr Met Ser Asn
            20                  25                  30

Arg Ala Leu Gln Arg Ser Ala Val Leu Ser Ala Phe Val Leu Leu Arg
        35                  40                  45

Ala Val Thr Gly Phe Ser Asp Gly Lys Ala Ile Trp Asp Lys Lys
    50                  55                  60

Gln Tyr Val Ser Pro Val Asn Pro Ser Gln Leu Phe Leu Tyr Asp Thr
65                  70                  75                  80

Phe Pro Lys Asn Phe Ser Trp Gly Val Gly Thr Gly Ala Phe Gln Val
                85                  90                  95

Glu Gly Ser Trp Lys Thr Asp Gly Arg Gly Pro Ser Ile Trp Asp Arg
            100                 105                 110

Tyr Val Tyr Ser His Leu Arg Gly Val Asn Gly Thr Asp Arg Ser Thr
        115                 120                 125

Asp Ser Tyr Ile Phe Leu Glu Lys Asp Leu Leu Ala Leu Asp Phe Leu
    130                 135                 140

Gly Val Ser Phe Tyr Gln Phe Ser Ile Ser Trp Pro Arg Leu Phe Pro
145                 150                 155                 160

Asn Gly Thr Val Ala Ala Val Asn Ala Gln Gly Leu Arg Tyr Tyr Arg
                165                 170                 175

Ala Leu Leu Asp Ser Leu Val Leu Arg Asn Ile Glu Pro Ile Val Thr
```

```
                    180             185              190
Leu Tyr His Trp Asp Leu Pro Leu Thr Leu Gln Glu Glu Tyr Gly Gly
            195                 200             205

Trp Lys Asn Ala Thr Met Ile Asp Leu Phe Asn Asp Tyr Ala Thr Tyr
            210                 215             220

Cys Phe Gln Thr Phe Gly Asp Arg Val Lys Tyr Trp Ile Thr Ile His
225                 230             235                 240

Asn Pro Tyr Leu Val Ala Trp His Gly Phe Gly Thr Gly Met His Ala
                245                 250             255

Pro Gly Glu Lys Gly Asn Leu Thr Ala Val Tyr Thr Val Gly His Asn
            260                 265             270

Leu Ile Lys Ala His Ser Lys Val Trp His Asn Tyr Asp Lys Asn Phe
            275                 280             285

Arg Pro His Gln Lys Gly Trp Leu Ser Ile Thr Leu Gly Ser His Trp
            290                 295             300

Ile Glu Pro Asn Arg Thr Asp Asn Met Glu Asp Val Ile Asn Cys Gln
305                 310             315                 320

His Ser Met Ser Ser Val Leu Gly Trp Phe Ala Asn Pro Ile His Gly
                325                 330             335

Asp Gly Asp Tyr Pro Glu Phe Met Lys Thr Gly Ala Met Ile Pro Glu
                340                 345             350

Phe Ser Glu Ala Glu Lys Glu Val Arg Gly Thr Ala Asp Phe Phe
            355                 360             365

Ala Phe Ser Phe Gly Pro Asn Asn Phe Arg Pro Ser Asn Thr Val Val
            370                 375             380

Lys Met Gly Gln Asn Val Ser Leu Asn Leu Arg Gln Val Leu Asn Trp
385                 390             395                 400

Ile Lys Leu Glu Tyr Asp Asp Pro Gln Ile Leu Ile Ser Glu Asn Gly
                405                 410             415

Trp Phe Thr Asp Ser Tyr Ile Lys Thr Glu Asp Thr Thr Ala Ile Tyr
                420                 425             430

Met Met Lys Asn Phe Leu Asn Gln Val Leu Gln Ala Ile Lys Phe Asp
            435                 440             445

Glu Ile Arg Val Phe Gly Tyr Thr Ala Trp Thr Leu Leu Asp Gly Phe
450                 455             460

Glu Trp Gln Asp Ala Tyr Thr Thr Arg Arg Gly Leu Phe Tyr Val Asp
465                 470             475                 480

Phe Asn Ser Glu Gln Lys Glu Arg Lys Pro Lys Ser Ser Ala His Tyr
                485                 490             495

Tyr Lys Gln Ile Ile Gln Asp Asn Gly Phe Pro Leu Lys Glu Ser Thr
            500                 505             510

Pro Asp Met Lys Gly Arg Phe Pro Cys Asp Phe Ser Trp Gly Val Thr
            515                 520             525

Glu Ser Val Leu Lys Pro Glu Phe Thr Val Ser Ser Pro Gln Phe Thr
            530                 535             540

Asp Pro His Leu Tyr Val Trp Asn Val Thr Gly Asn Arg Leu Leu Tyr
545                 550             555             560

Arg Val Glu Gly Val Arg Leu Lys Thr Arg Pro Ser Gln Cys Thr Asp
                565                 570             575

Tyr Val Ser Ile Lys Lys Arg Val Glu Met Leu Ala Lys Met Lys Val
            580                 585             590

Thr His Tyr Gln Phe Ala Leu Asp Trp Thr Ser Ile Leu Pro Thr Gly
            595                 600             605
```

-continued

Asn Leu Ser Lys Val Asn Arg Gln Val Leu Arg Tyr Tyr Arg Cys Val
610                 615                 620

Val Ser Glu Gly Leu Lys Leu Gly Val Phe Pro Met Val Thr Leu Tyr
625                 630                 635                 640

His Pro Thr His Ser His Leu Gly Leu Pro Leu Pro Leu Leu Ser Ser
                645                 650                 655

Gly Gly Trp Leu Asn Met Asn Thr Ala Lys Ala Phe Gln Asp Tyr Ala
            660                 665                 670

Glu Leu Cys Phe Arg Glu Leu Gly Asp Leu Val Lys Leu Trp Ile Thr
        675                 680                 685

Ile Asn Glu Pro Asn Arg Leu Ser Asp Met Tyr Asn Arg Thr Ser Asn
690                 695                 700

Asp Thr Tyr Arg Ala Ala His Asn Leu Met Ile Ala His Ala Gln Val
705                 710                 715                 720

Trp His Leu Tyr Asp Arg Gln Tyr Arg Pro Val Gln His Gly Ala Val
                725                 730                 735

Ser Leu Ser Leu His Cys Asp Trp Ala Glu Pro Ala Asn Pro Phe Val
            740                 745                 750

Asp Ser His Trp Lys Ala Ala Glu Arg Phe Leu Gln Phe Glu Ile Ala
        755                 760                 765

Trp Phe Ala Asp Pro Leu Phe Lys Thr Gly Asp Tyr Pro Ser Val Met
770                 775                 780

Lys Glu Tyr Ile Ala Ser Lys Asn Gln Arg Gly Leu Ser Ser Ser Val
785                 790                 795                 800

Leu Pro Arg Phe Thr Ala Lys Glu Ser Arg Leu Val Lys Gly Thr Val
                805                 810                 815

Asp Phe Tyr Ala Leu Asn His Phe Thr Thr Arg Phe Val Ile His Lys
            820                 825                 830

Gln Leu Asn Thr Asn Arg Ser Val Ala Asp Arg Asp Val Gln Phe Leu
        835                 840                 845

Gln Asp Ile Thr Arg Leu Ser Ser Pro Ser Arg Leu Ala Val Thr Pro
850                 855                 860

Trp Gly Val Arg Lys Leu Leu Ala Trp Ile Arg Arg Asn Tyr Arg Asp
865                 870                 875                 880

Arg Asp Ile Tyr Ile Thr Ala Asn Gly Ile Asp Asp Leu Ala Leu Glu
                885                 890                 895

Asp Asp Gln Ile Arg Lys Tyr Tyr Leu Glu Lys Tyr Val Gln Glu Ala
            900                 905                 910

Leu Lys Ala Tyr Leu Ile Asp Lys Val Lys Ile Lys Gly Tyr Tyr Ala
        915                 920                 925

Phe Lys Leu Thr Glu Glu Lys Ser Lys Pro Arg Phe Gly Phe Phe Thr
930                 935                 940

Ser Asp Phe Arg Ala Lys Ser Ser Val Gln Phe Tyr Ser Lys Leu Ile
945                 950                 955                 960

Ser Ser Ser Gly Leu Pro Ala Glu Asn Arg Ser Pro Ala Cys Gly Gln
                965                 970                 975

Pro Ala Glu Asp Thr Asp Cys Thr Ile Cys Ser Phe Leu Val Glu Lys
            980                 985                 990

Lys Pro Leu Ile Phe Gly Cys Cys Phe Ile Ser Thr Leu Ala Val
        995                 1000                1005

Leu Leu Ser Ile Thr Val Phe His His Gln Lys Arg Arg Lys Phe
    1010                1015                1020

Gln Lys Ala Arg Asn Leu Gln Asn Ile Pro Leu Lys Lys Gly His
    1025                1030                1035

```
Ser Arg Val Phe Ser
        1040

<210> SEQ ID NO 3
<211> LENGTH: 992
<212> TYPE: PRT
<213> ORGANISM: Artificial Sequence
<220> FEATURE:
<223> OTHER INFORMATION: Synthetic mutation

<400> SEQUENCE: 3

Met Lys Thr Gly Cys Ala Ala Gly Ser Pro Gly Asn Glu Trp Ile Phe
1               5                   10                  15

Phe Ser Ser Asp Glu Arg Asn Thr Arg Ser Arg Lys Thr Met Ser Asn
                20                  25                  30

Arg Ala Leu Gln Arg Ser Ala Val Leu Ser Ala Phe Val Leu Leu Arg
            35                  40                  45

Ala Val Thr Gly Phe Ser Gly Asp Gly Lys Ala Ile Trp Asp Lys Lys
        50                  55                  60

Gln Tyr Val Ser Pro Val Asn Pro Ser Gln Leu Phe Leu Tyr Asp Thr
65                  70                  75                  80

Phe Pro Lys Asn Phe Ser Trp Gly Val Gly Thr Gly Ala Phe Gln Val
                85                  90                  95

Glu Gly Ser Trp Lys Thr Asp Gly Arg Gly Pro Ser Ile Trp Asp Arg
            100                 105                 110

Tyr Val Tyr Ser His Leu Arg Gly Val Asn Gly Thr Asp Arg Ser Thr
        115                 120                 125

Asp Ser Tyr Ile Phe Leu Glu Lys Asp Leu Leu Ala Leu Asp Phe Leu
130                 135                 140

Gly Val Ser Phe Tyr Gln Phe Ser Ile Ser Trp Pro Arg Leu Phe Pro
145                 150                 155                 160

Asn Gly Thr Val Ala Ala Val Asn Ala Gln Gly Leu Arg Tyr Tyr Arg
                165                 170                 175

Ala Leu Leu Asp Ser Leu Val Leu Arg Asn Ile Glu Pro Ile Val Thr
            180                 185                 190

Leu Tyr His Trp Asp Leu Pro Leu Thr Leu Gln Glu Glu Tyr Gly Gly
        195                 200                 205

Trp Lys Asn Ala Thr Met Ile Asp Leu Phe Asn Asp Tyr Ala Thr Tyr
        210                 215                 220

Cys Phe Gln Thr Phe Gly Asp Arg Val Lys Tyr Trp Ile Thr Ile His
225                 230                 235                 240

Asn Pro Tyr Leu Val Ala Trp His Gly Phe Gly Thr Gly Met His Ala
                245                 250                 255

Pro Gly Glu Lys Gly Asn Leu Thr Ala Val Tyr Thr Val Gly His Asn
            260                 265                 270

Leu Ile Lys Ala His Ser Lys Val Trp His Asn Tyr Asp Lys Asn Phe
        275                 280                 285

Arg Pro His Gln Lys Gly Trp Leu Ser Ile Thr Leu Gly Ser His Trp
    290                 295                 300

Ile Glu Pro Asn Arg Thr Asp Asn Met Glu Asp Val Ile Asn Cys Gln
305                 310                 315                 320

His Ser Met Ser Ser Val Leu Gly Trp Phe Ala Asn Pro Ile His Gly
                325                 330                 335

Asp Gly Asp Tyr Pro Glu Phe Met Lys Thr Gly Ala Met Ile Pro Glu
            340                 345                 350
```

-continued

Phe Ser Glu Ala Glu Lys Glu Val Arg Gly Thr Ala Asp Phe Phe
        355                 360                 365

Ala Phe Ser Phe Gly Pro Asn Asn Phe Arg Pro Ser Asn Thr Val Val
370                 375                 380

Lys Met Gly Gln Asn Val Ser Leu Asn Leu Arg Gln Val Leu Asn Trp
385                 390                 395                 400

Ile Lys Leu Glu Tyr Asp Asp Pro Gln Ile Leu Ile Ser Glu Asn Gly
            405                 410                 415

Trp Phe Thr Asp Ser Tyr Ile Lys Thr Glu Asp Thr Ala Ile Tyr
            420                 425                 430

Met Met Lys Asn Phe Leu Asn Gln Val Leu Gln Ala Ile Lys Phe Asp
            435                 440                 445

Glu Ile Arg Val Phe Gly Tyr Thr Ala Trp Thr Leu Leu Asp Gly Phe
450                 455                 460

Glu Trp Gln Asp Ala Tyr Thr Thr Arg Arg Gly Leu Phe Tyr Val Asp
465                 470                 475                 480

Phe Asn Ser Glu Gln Lys Glu Arg Lys Pro Lys Ser Ser Ala His Tyr
                485                 490                 495

Tyr Lys Gln Ile Ile Gln Asp Asn Gly Phe Pro Leu Lys Glu Ser Thr
            500                 505                 510

Pro Asp Met Lys Gly Arg Phe Pro Cys Asp Phe Ser Trp Gly Val Thr
            515                 520                 525

Glu Ser Val Leu Lys Pro Glu Phe Thr Val Ser Ser Pro Gln Phe Thr
530                 535                 540

Asp Pro His Leu Tyr Val Trp Asn Val Thr Gly Asn Arg Leu Leu Tyr
545                 550                 555                 560

Arg Val Glu Gly Val Arg Leu Lys Thr Arg Pro Ser Gln Cys Thr Asp
                565                 570                 575

Tyr Val Ser Ile Lys Lys Arg Val Glu Met Leu Ala Lys Met Lys Val
            580                 585                 590

Thr His Tyr Gln Phe Ala Leu Asp Trp Thr Ser Ile Leu Pro Thr Gly
            595                 600                 605

Asn Leu Ser Lys Val Asn Arg Gln Val Leu Arg Tyr Tyr Arg Cys Val
610                 615                 620

Val Ser Glu Gly Leu Lys Leu Gly Val Phe Pro Met Val Thr Leu Tyr
625                 630                 635                 640

His Pro Thr His Ser His Leu Gly Leu Pro Leu Pro Leu Leu Ser Ser
                645                 650                 655

Gly Gly Trp Leu Asn Met Asn Thr Ala Lys Ala Phe Gln Asp Tyr Ala
            660                 665                 670

Glu Leu Cys Phe Arg Glu Leu Gly Asp Leu Val Lys Leu Trp Ile Thr
            675                 680                 685

Ile Asn Glu Pro Asn Arg Leu Ser Asp Met Tyr Asn Arg Thr Ser Asn
690                 695                 700

Asp Thr Tyr Arg Ala Ala His Asn Leu Met Ile Ala His Ala Gln Val
705                 710                 715                 720

Trp His Leu Tyr Asp Arg Gln Tyr Arg Pro Val Gln His Gly Ala Val
                725                 730                 735

Ser Leu Ser Leu His Cys Asp Trp Ala Glu Pro Ala Asn Pro Phe Val
            740                 745                 750

Asp Ser His Trp Lys Ala Ala Glu Arg Phe Leu Gln Phe Glu Ile Ala
            755                 760                 765

Trp Phe Ala Asp Pro Leu Phe Lys Thr Gly Asp Tyr Pro Ser Val Met
770                 775                 780

```
Lys Glu Tyr Ile Ala Ser Lys Asn Gln Arg Gly Leu Ser Ser Val
785                 790                 795                 800

Leu Pro Arg Phe Thr Ala Lys Glu Ser Arg Leu Val Lys Gly Thr Val
            805                 810                 815

Asp Phe Tyr Ala Leu Asn His Phe Thr Thr Arg Phe Val Ile His Lys
            820                 825                 830

Gln Leu Asn Thr Asn Arg Ser Val Ala Asp Arg Asp Val Gln Phe Leu
            835                 840                 845

Gln Asp Ile Thr Arg Leu Ser Ser Pro Ser Arg Leu Ala Val Thr Pro
            850                 855                 860

Trp Gly Val Arg Lys Leu Leu Ala Trp Ile Arg Arg Asn Tyr Arg Asp
865                 870                 875                 880

Arg Asp Ile Tyr Ile Thr Ala Asn Gly Ile Asp Leu Ala Leu Glu
            885                 890                 895

Asp Asp Gln Ile Arg Lys Tyr Tyr Leu Glu Lys Tyr Val Gln Glu Ala
            900                 905                 910

Leu Lys Ala Tyr Leu Ile Asp Lys Val Lys Ile Lys Gly Tyr Tyr Ala
            915                 920                 925

Phe Lys Leu Thr Glu Glu Lys Ser Lys Pro Arg Phe Gly Phe Phe Thr
            930                 935                 940

Ser Asp Phe Arg Ala Lys Ser Ser Val Gln Phe Tyr Ser Lys Leu Ile
945                 950                 955                 960

Ser Ser Ser Gly Leu Pro Ala Glu Asn Arg Ser Pro Ala Cys Gly Gln
            965                 970                 975

Pro Ala Glu Asp Thr Asp Cys Thr Ile Cys Ser Phe Leu Val Glu Lys
            980                 985                 990

<210> SEQ ID NO 4
<211> LENGTH: 8
<212> TYPE: PRT
<213> ORGANISM: Artificial Sequence
<220> FEATURE:
<223> OTHER INFORMATION: Synthetic mutation

<400> SEQUENCE: 4

Asp Tyr Lys Asp Asp Asp Asp Lys
1               5

<210> SEQ ID NO 5
<211> LENGTH: 19
<212> TYPE: PRT
<213> ORGANISM: Artificial Sequence
<220> FEATURE:
<223> OTHER INFORMATION: Synthetic mutation

<400> SEQUENCE: 5

Gly Pro Arg Phe Glu Gly Lys Pro Ile Pro Asn Pro Leu Leu Gly Leu
1               5                   10                  15

Asp Ser Thr

<210> SEQ ID NO 6
<211> LENGTH: 6
<212> TYPE: PRT
<213> ORGANISM: Artificial Sequence
<220> FEATURE:
<223> OTHER INFORMATION: Synthetic mutation

<400> SEQUENCE: 6

His His His His His His
1               5
```

<210> SEQ ID NO 7
<211> LENGTH: 3135
<212> TYPE: DNA
<213> ORGANISM: human

<400> SEQUENCE: 7

| | | | | | |
|---|---|---|---|---|---|
| atgaagccag | gctgtgcggc | aggatctcca | gggaatgaat | ggattttctt | cagcactgat | 60 |
| gaaataacca | cacgctatag | aatacaatg | tccaacgggg | gattgcaaag | atctgtcatc | 120 |
| ctgtcagcac | ttattctgct | acgagctgtt | actggattct | ctggagatgg | aagagctata | 180 |
| tggtctaaaa | atcctaattt | tactccggta | aatgaaagtc | agctgttcct | ctatgacact | 240 |
| ttccctaaaa | acttttctg | gggtattggg | actggagcat | tgcaagtgga | agggagttgg | 300 |
| aagaaggatg | gaaaaggacc | ttctatatgg | gatcatttca | tccacacaca | ccttaaaaat | 360 |
| gtcagcagca | cgaatggttc | cagtgacagt | tatattttc | tggaaaaaga | cttatcagcc | 420 |
| ctggattta | taggagtttc | ttttttatcaa | ttttcaattt | cctggccaag | gcttttcccc | 480 |
| gatggaatag | taacagttgc | caacgcaaaa | ggtctgcagt | actacagtac | tcttctggac | 540 |
| gctctagtgc | ttagaaacat | tgaacctata | gttactttat | accactggga | tttgcctttg | 600 |
| gcactacaag | aaaaatatgg | ggggtggaaa | aatgatacca | aatagatat | cttcaatgac | 660 |
| tatgccacat | actgtttcca | gatgtttggg | gaccgtgtca | aatattggat | tacaattcac | 720 |
| aacccatatc | tagtggcttg | gcatgggtat | gggacaggta | tgcatgcccc | tggagagaag | 780 |
| ggaaatttag | cagctgtcta | cactgtggga | cacaacttga | tcaaggctca | ctcgaaagtt | 840 |
| tggcataact | acaacacaca | tttccgccca | catcagaagg | gttggttatc | gatcacgttg | 900 |
| ggatctcatt | ggatcgagcc | aaaccggtcg | gaaaacacga | tggatatatt | caaatgtcaa | 960 |
| caatccatgg | tttctgtgct | tggatggttt | gccaacccta | tccatgggga | tggcgactat | 1020 |
| ccagagggga | tgagaaagaa | gttgttctcc | gttctaccca | tttctctga | gcagagaag | 1080 |
| catgagatga | gaggcacagc | tgatttcttt | gccttttctt | ttggacccaa | caacttcaag | 1140 |
| ccccctaaaca | ccatggctaa | aatgggacaa | aatgtttcac | ttaatttaag | agaagcgctg | 1200 |
| aactggatta | aactggaata | caacaaccct | cgaatcttga | ttgctgagaa | tggctggttc | 1260 |
| acagacagtc | gtgtgaaaac | agaagacacc | acggccatct | acatgatgaa | gaatttcctc | 1320 |
| agccaggtgc | ttcaagcaat | aaggttagat | gaaatacgag | tgtttggtta | tactgcctgg | 1380 |
| tctctcctgg | atggctttga | atggcaggat | gcttacacca | tccgccgagg | attatttat | 1440 |
| gtggattta | acagtaaaca | gaaagagcgg | aaacctaagt | cttcagcaca | ctactacaaa | 1500 |
| cagatcatac | gagaaaatgg | tttttcttta | aaagagtcca | cgccagatgt | gcagggccag | 1560 |
| tttccctgtg | acttctcctg | gggtgtcact | gaatctgttc | ttaagcccga | gtctgtggct | 1620 |
| tcgtccccac | agttcagcga | tcctcatctg | tacgtgtgga | acgccactgg | caacagactg | 1680 |
| ttgcaccgag | tggaaggggt | gaggctgaaa | acacgacccg | ctcaatgcac | agatttgta | 1740 |
| aacatcaaaa | aacaacttga | gatgttggca | agaatgaaag | tcacccacta | ccggtttgct | 1800 |
| ctggattggg | cctcggtcct | tcccactggc | aacctgtccg | cggtgaaccg | acaggccctg | 1860 |
| aggtactaca | ggtgcgtggt | cagtgagggg | ctgaagcttg | gcatctccgc | gatggtcacc | 1920 |
| ctgtattatc | cgacccacgc | ccacctaggc | ctccccgagc | tctgttgca | tgccgacggg | 1980 |
| tggctgaacc | catcgacggc | cgaggccttc | caggcctacg | ctgggctgtg | cttccaggag | 2040 |
| ctgggggacc | tggtgaagct | ctggatcacc | atcaacgagc | ctaaccggct | aagtgacatc | 2100 |
| tacaaccgct | ctggcaacga | cacctacggg | gcggcgcaca | acctgctggt | ggcccacgcc | 2160 |

```
ctggcctggc gcctctacga ccggcagttc aggccctcac agcgcgggc cgtgtcgctg      2220 tcgctgcacg cggactgggc ggaacccgcc aaccccctatg ctgactcgca ctggagggcg    2280
gccgagcgct tcctgcagtt cgagatcgcc tggttcgccg agccgctctt caagaccggg    2340
gactaccccg cggccatgag ggaatacatt gcctccaagc accgacgggg gctttccagc    2400
tcggccctgc cgcgcctcac cgaggccgaa aggaggctgc tcaagggcac ggtcgacttc    2460
tgcgcgctca accacttcac cactaggttc gtgatgcacg agcagctggc cggcagccgc    2520
tacgactcgg acagggacat ccagtttctg caggacatca cccgcctgag ctcccccacg    2580
cgcctggctg tgattccctg gggggtgcgc aagctgctgc ggtgggtccg gaggaactac    2640
ggcgacatgg acatttacat caccgccagt ggcatcgacg accaggctct ggaggatgac    2700
cggctccgga agtactacct agggaagtac cttcaggagg tgctgaaagc ataccctgatt   2760 gataaagtca gaatcaaagg ctattatgca ttcaaactgg ctgaagagaa atctaaaccc    2820
agatttggat tcttcacatc tgattttaaa gctaaatcct caatacaatt ttacaacaaa    2880
gtgatcagca gcaggggctt ccctttgag aacagtagtt ctagatgcag tcagacccaa      2940
gaaaatacag agtgcactgt ctgcttattc cttgtgcaga agaaaccact gatattcctg    3000
ggttgttgct tcttctccac cctggttcta ctcttatcaa ttgccattt tcaaaggcag       3060 aagagaagaa agttttggaa agcaaaaaac ttacaacaca taccattaaa gaaaggcaag    3120
agagttgtta gctaa                                                     3135
```

```
<210> SEQ ID NO 8
<211> LENGTH: 1044
<212> TYPE: PRT
<213> ORGANISM: human

<400> SEQUENCE: 8
```

```
Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
        35                  40                  45

Ala Val Thr Gly Phe Ser Gly Asp Gly Arg Ala Ile Trp Ser Lys Asn
    50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
```

-continued

```
            195                 200                 205
Trp Lys Asn Asp Thr Ile Ile Asp Ile Phe Asn Asp Tyr Ala Thr Tyr
210                 215                 220
Cys Phe Gln Met Phe Gly Asp Arg Val Lys Tyr Trp Ile Thr Ile His
225                 230                 235                 240
Asn Pro Tyr Leu Val Ala Trp His Gly Tyr Gly Thr Gly Met His Ala
                    245                 250                 255
Pro Gly Glu Lys Gly Asn Leu Ala Ala Val Tyr Thr Val Gly His Asn
                260                 265                 270
Leu Ile Lys Ala His Ser Lys Val Trp His Asn Tyr Asn Thr His Phe
            275                 280                 285
Arg Pro His Gln Lys Gly Trp Leu Ser Ile Thr Leu Gly Ser His Trp
290                 295                 300
Ile Glu Pro Asn Arg Ser Glu Asn Thr Met Asp Ile Phe Lys Cys Gln
305                 310                 315                 320
Gln Ser Met Val Ser Val Leu Gly Trp Phe Ala Asn Pro Ile His Gly
                    325                 330                 335
Asp Gly Asp Tyr Pro Glu Gly Met Arg Lys Lys Leu Phe Ser Val Leu
                340                 345                 350
Pro Ile Phe Ser Glu Ala Glu Lys His Glu Met Arg Gly Thr Ala Asp
            355                 360                 365
Phe Phe Ala Phe Ser Phe Gly Pro Asn Asn Phe Lys Pro Leu Asn Thr
370                 375                 380
Met Ala Lys Met Gly Gln Asn Val Ser Leu Asn Leu Arg Glu Ala Leu
385                 390                 395                 400
Asn Trp Ile Lys Leu Glu Tyr Asn Asn Pro Arg Ile Leu Ile Ala Glu
                    405                 410                 415
Asn Gly Trp Phe Thr Asp Ser Arg Val Lys Thr Glu Asp Thr Thr Ala
                420                 425                 430
Ile Tyr Met Met Lys Asn Phe Leu Ser Gln Val Leu Gln Ala Ile Arg
            435                 440                 445
Leu Asp Glu Ile Arg Val Phe Gly Tyr Thr Ala Trp Ser Leu Leu Asp
450                 455                 460
Gly Phe Glu Trp Gln Asp Ala Tyr Thr Ile Arg Arg Gly Leu Phe Tyr
465                 470                 475                 480
Val Asp Phe Asn Ser Lys Gln Lys Glu Arg Lys Pro Lys Ser Ser Ala
                    485                 490                 495
His Tyr Tyr Lys Gln Ile Ile Arg Glu Asn Gly Phe Ser Leu Lys Glu
                500                 505                 510
Ser Thr Pro Asp Val Gln Gly Gln Phe Pro Cys Asp Phe Ser Trp Gly
            515                 520                 525
Val Thr Glu Ser Val Leu Lys Pro Glu Ser Val Ala Ser Ser Pro Gln
530                 535                 540
Phe Ser Asp Pro His Leu Tyr Val Trp Asn Ala Thr Gly Asn Arg Leu
545                 550                 555                 560
Leu His Arg Val Glu Gly Val Arg Leu Lys Thr Arg Pro Ala Gln Cys
                    565                 570                 575
Thr Asp Phe Val Asn Ile Lys Lys Gln Leu Glu Met Leu Ala Arg Met
                580                 585                 590
Lys Val Thr His Tyr Arg Phe Ala Leu Asp Trp Ala Ser Val Leu Pro
            595                 600                 605
Thr Gly Asn Leu Ser Ala Val Asn Arg Gln Ala Leu Arg Tyr Tyr Arg
610                 615                 620
```

-continued

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
        645                 650                 655

His Ala Asp Gly Trp Leu Asn Pro Ser Thr Ala Glu Ala Phe Gln Ala
            660                 665                 670

Tyr Ala Gly Leu Cys Phe Gln Glu Leu Gly Asp Leu Val Lys Leu Trp
            675                 680                 685

Ile Thr Ile Asn Glu Pro Asn Arg Leu Ser Asp Ile Tyr Asn Arg Ser
690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
            755                 760                 765

Ile Ala Trp Phe Ala Glu Pro Leu Phe Lys Thr Gly Asp Tyr Pro Ala
770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Leu Leu Lys Gly
                805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
835                 840                 845

Phe Leu Gln Asp Ile Thr Arg Leu Ser Ser Pro Thr Arg Leu Ala Val
850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Gln Ala
            885                 890                 895

Leu Glu Asp Asp Arg Leu Arg Lys Tyr Tyr Leu Gly Lys Tyr Leu Gln
                900                 905                 910

Glu Val Leu Lys Ala Tyr Leu Ile Asp Lys Val Arg Ile Lys Gly Tyr
            915                 920                 925

Tyr Ala Phe Lys Leu Ala Glu Glu Lys Ser Lys Pro Arg Phe Gly Phe
    930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Arg Cys
                965                 970                 975

Ser Gln Thr Gln Glu Asn Thr Glu Cys Thr Val Cys Leu Phe Leu Val
            980                 985                 990

Gln Lys Lys Pro Leu Ile Phe Leu Gly Cys Cys Phe Phe Ser Thr Leu
                995                 1000                1005

Val Leu Leu Leu Ser Ile Ala Ile Phe Gln Arg Gln Lys Arg Arg
    1010                1015                1020

Lys Phe Trp Lys Ala Lys Asn Leu Gln His Ile Pro Leu Lys Lys
    1025                1030                1035

Gly Lys Arg Val Val Ser
    1040

<210> SEQ ID NO 9
<211> LENGTH: 994
<212> TYPE: PRT
<213> ORGANISM: Artificial Sequence
<220> FEATURE:
<223> OTHER INFORMATION: Synthetic mutation

<400> SEQUENCE: 9

```
Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
        35                  40                  45

Ala Val Thr Gly Phe Ser Gly Asp Gly Arg Ala Ile Trp Ser Lys Asn
50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
        355                 360                 365
```

```
            Phe Phe Ala Phe Ser Phe Gly Pro Asn Asn Phe Lys Pro Leu Asn Thr
                370                 375                 380

Met Ala Lys Met Gly Gln Asn Val Ser Leu Asn Leu Arg Glu Ala Leu
            385                 390                 395                 400

Asn Trp Ile Lys Leu Glu Tyr Asn Asn Pro Arg Ile Leu Ile Ala Glu
                            405                 410                 415

Asn Gly Trp Phe Thr Asp Ser Arg Val Lys Thr Glu Asp Thr Thr Ala
                        420                 425                 430

Ile Tyr Met Met Lys Asn Phe Leu Ser Gln Val Leu Gln Ala Ile Arg
                    435                 440                 445

Leu Asp Glu Ile Arg Val Phe Gly Tyr Thr Ala Trp Ser Leu Leu Asp
                450                 455                 460

Gly Phe Glu Trp Gln Asp Ala Tyr Thr Ile Arg Arg Gly Leu Phe Tyr
            465                 470                 475                 480

Val Asp Phe Asn Ser Lys Gln Lys Glu Arg Lys Pro Lys Ser Ser Ala
                            485                 490                 495

His Tyr Tyr Lys Gln Ile Ile Arg Glu Asn Gly Phe Ser Leu Lys Glu
                        500                 505                 510

Ser Thr Pro Asp Val Gln Gly Gln Phe Pro Cys Asp Phe Ser Trp Gly
                    515                 520                 525

Val Thr Glu Ser Val Leu Lys Pro Glu Ser Val Ala Ser Ser Pro Gln
                530                 535                 540

Phe Ser Asp Pro His Leu Tyr Val Trp Asn Ala Thr Gly Asn Arg Leu
            545                 550                 555                 560

Leu His Arg Val Glu Gly Val Arg Leu Lys Thr Arg Pro Ala Gln Cys
                            565                 570                 575

Thr Asp Phe Val Asn Ile Lys Lys Gln Leu Glu Met Leu Ala Arg Met
                        580                 585                 590

Lys Val Thr His Tyr Arg Phe Ala Leu Asp Trp Ala Ser Val Leu Pro
                    595                 600                 605

Thr Gly Asn Leu Ser Ala Val Asn Arg Gln Ala Leu Arg Tyr Tyr Arg
                610                 615                 620

Cys Val Val Ser Glu Gly Leu Lys Leu Gly Ile Ser Ala Met Val Thr
            625                 630                 635                 640

Leu Tyr Tyr Pro Thr His Ala His Leu Gly Leu Pro Glu Pro Leu Leu
                            645                 650                 655

His Ala Asp Gly Trp Leu Asn Pro Ser Thr Ala Glu Ala Phe Gln Ala
                        660                 665                 670

Tyr Ala Gly Leu Cys Phe Gln Glu Leu Gly Asp Leu Val Lys Leu Trp
                    675                 680                 685

Ile Thr Ile Asn Glu Pro Asn Arg Leu Ser Asp Ile Tyr Asn Arg Ser
                690                 695                 700

Gly Asn Asp Thr Tyr Gly Ala Ala His Asn Leu Leu Val Ala His Ala
            705                 710                 715                 720

Leu Ala Trp Arg Leu Tyr Asp Arg Gln Phe Arg Pro Ser Gln Arg Gly
                            725                 730                 735

Ala Val Ser Leu Ser Leu His Ala Asp Trp Ala Glu Pro Ala Asn Pro
                        740                 745                 750

Tyr Ala Asp Ser His Trp Arg Ala Ala Glu Arg Phe Leu Gln Phe Glu
                    755                 760                 765

Ile Ala Trp Phe Ala Glu Pro Leu Phe Lys Thr Gly Asp Tyr Pro Ala
                770                 775                 780

Ala Met Arg Glu Tyr Ile Ala Ser Lys His Arg Arg Gly Leu Ser Ser
            785                 790                 795                 800
```

```
Ser Ala Leu Pro Arg Leu Thr Glu Ala Glu Arg Arg Leu Leu Lys Gly
            805                 810                 815
Thr Val Asp Phe Cys Ala Leu Asn His Phe Thr Thr Arg Phe Val Met
            820                 825                 830
His Glu Gln Leu Ala Gly Ser Arg Tyr Asp Ser Asp Arg Asp Ile Gln
            835                 840                 845
Phe Leu Gln Asp Ile Thr Arg Leu Ser Ser Pro Thr Arg Leu Ala Val
850                 855                 860
Ile Pro Trp Gly Val Arg Lys Leu Leu Arg Trp Val Arg Arg Asn Tyr
865                 870                 875                 880
Gly Asp Met Asp Ile Tyr Ile Thr Ala Ser Gly Ile Asp Asp Gln Ala
            885                 890                 895
Leu Glu Asp Asp Arg Leu Arg Lys Tyr Tyr Leu Gly Lys Tyr Leu Gln
            900                 905                 910
Glu Val Leu Lys Ala Tyr Leu Ile Asp Lys Val Arg Ile Lys Gly Tyr
            915                 920                 925
Tyr Ala Phe Lys Leu Ala Glu Glu Lys Ser Lys Pro Arg Phe Gly Phe
            930                 935                 940
Phe Thr Ser Asp Phe Lys Ala Lys Ser Ser Ile Gln Phe Tyr Asn Lys
945                 950                 955                 960
Val Ile Ser Ser Arg Gly Phe Pro Phe Glu Asn Ser Ser Ser Arg Cys
            965                 970                 975
Ser Gln Thr Gln Glu Asn Thr Glu Cys Thr Val Cys Leu Phe Leu Val
            980                 985                 990
Gln Lys
```